US011110458B2

(12) United States Patent
Carman et al.

(10) Patent No.: US 11,110,458 B2
(45) Date of Patent: Sep. 7, 2021

(54) SYSTEM FOR DETECTION OF SPACED DROPLETS

(71) Applicant: Bio-Rad Laboratories, Inc., Hercules, CA (US)

(72) Inventors: George Carman, Livermore, CA (US); Thomas H. Cauley, III, Pleasanton, CA (US); David P. Stumbo, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1057 days.

(21) Appl. No.: 14/171,766

(22) Filed: Feb. 3, 2014

(65) Prior Publication Data

US 2014/0221239 A1 Aug. 7, 2014

Related U.S. Application Data

(60) Provisional application No. 61/759,774, filed on Feb. 1, 2013.

(51) Int. Cl.
*C12Q 1/68* (2018.01)
*B01L 3/00* (2006.01)

(52) U.S. Cl.
CPC . *B01L 3/502784* (2013.01); *B01L 2200/0647* (2013.01); *B01L 2200/0673* (2013.01); *B01L 2300/0816* (2013.01); *B01L 2300/0867* (2013.01); *B01L 2400/0487* (2013.01)

(58) Field of Classification Search
CPC ....... B01L 3/502784; B01L 2200/0673; B01L 2400/0487; B01L 2300/0867
See application file for complete search history.

(56) References Cited

U.S. PATENT DOCUMENTS

| | | | | |
|---|---|---|---|---|
| 4,676,898 | A * | 6/1987 | Saxena | B01D 15/14 210/198.2 |
| 6,797,056 | B2 * | 9/2004 | David | C30B 7/00 117/201 |
| 7,294,503 | B2 | 11/2007 | Quake et al. | |
| 7,641,862 | B2 * | 1/2010 | Noetzel | B01L 3/502746 422/412 |
| 8,241,571 | B2 | 8/2012 | Goix et al. | |
| 2006/0072177 | A1 | 4/2006 | Putnam et al. | |
| 2008/0003142 | A1 | 1/2008 | Link et al. | |
| 2008/0014589 | A1 | 1/2008 | Link et al. | |
| 2009/0014360 | A1 | 1/2009 | Toner et al. | |
| 2009/0056116 | A1 | 3/2009 | Presley et al. | |
| 2010/0015606 | A1 | 1/2010 | Davies et al. | |
| 2010/0285975 | A1 | 11/2010 | Mathies et al. | |
| 2011/0217736 | A1 | 9/2011 | Hindson | |
| 2011/0223314 | A1 | 9/2011 | Zhang et al. | |
| 2011/0250597 | A1 | 10/2011 | Larson et al. | |
| 2011/0311978 | A1 * | 12/2011 | Makarewicz, Jr. | B01F 3/0807 435/6.12 |
| 2012/0208241 | A1 | 8/2012 | Link | |
| 2014/0179544 | A1 | 6/2014 | Steenblock et al. | |

FOREIGN PATENT DOCUMENTS

WO WO-2012081983 A1 * 6/2012 ............ B01D 15/22

OTHER PUBLICATIONS

Shane Thomas, Authorized Officer, International Searching Authority, U.S. Patent and Trademark Office, "International Search Report" in connection with related PCT Patent Application No. PCT/US2014/014516, dated May 7, 2014, 2 pages.

Shane Thomas, Authorized Officer, International Searching Authority, U.S. Patent and Trademark Office, "Written Opinion of the International Searching Authority" in connection with related PCT Patent Application No. PCT/US2014/014516, dated May 7, 2014, 6 pages.

* cited by examiner

*Primary Examiner* — Sahana S Kaup
(74) *Attorney, Agent, or Firm* — Kolisch Hartwell, P.C.

(57) ABSTRACT

System, including methods and apparatus, for spacing droplets from each other and for detection of spaced droplets.

9 Claims, 12 Drawing Sheets

Fig. 14

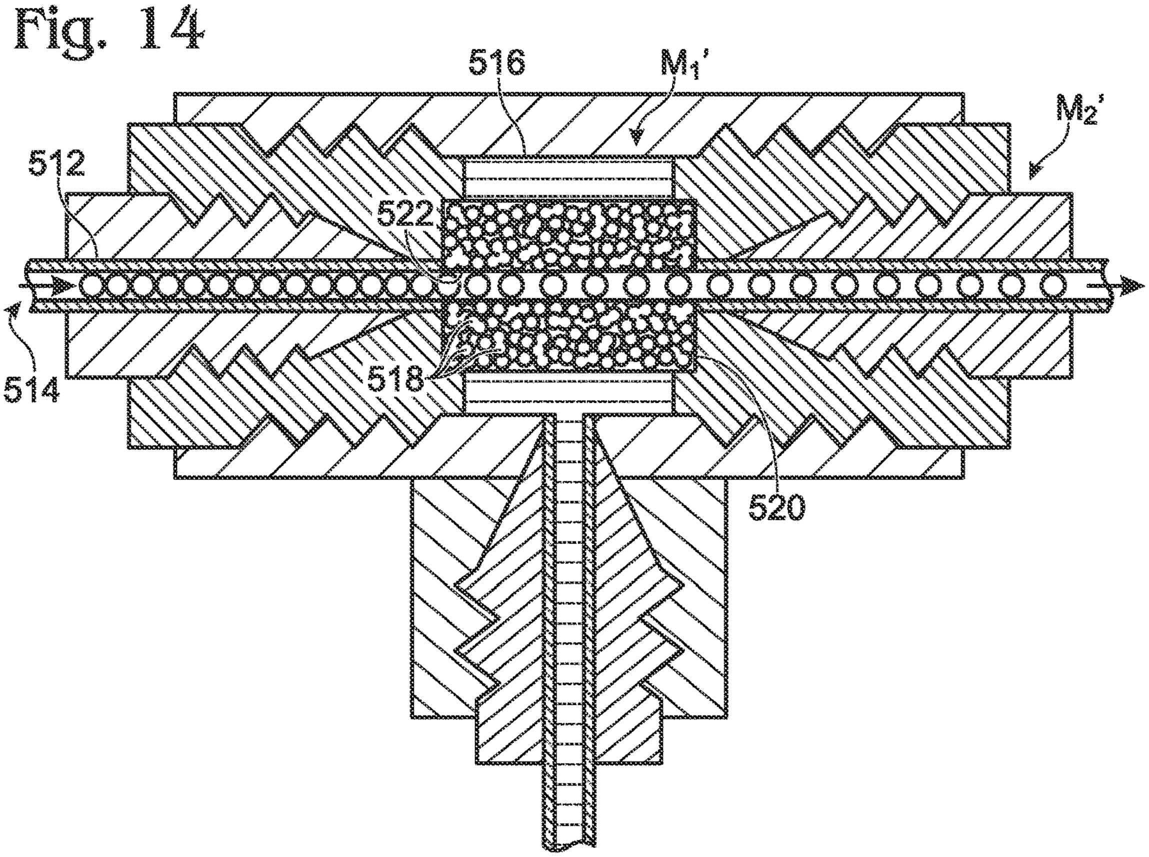

Fig. 16

600

602 TRANSPORTING DROPLETS OF A SAMPLE FLUID SUSPENDED IN A CARRIER FLUID INTO A DROPLET CHANNEL

↓

604 TRANSPORTING THE DROPLETS DOWNSTREAM THROUGH THE DROPLET CHANNEL

↓

606 TRANSPORTING DILUTION FLUID INTO A SHELL SURROUNDING THE DROPLET CHANNEL

↓

608 TRANSPORTING DILUTION FLUID FROM THE SHELL INTO THE DROPLET CHANNEL AT A CONTROLLED RATE

↓

610 TRANSPORTING THE DROPLETS TO A DETECTION REGION

↓

612 DETECTING FLUORESCENT RADIATION EMITTED BY DROPLETS PASSING THROUGH THE DETECTION REGION

SYSTEM FOR DETECTION OF SPACED DROPLETS

CROSS-REFERENCE TO PRIORITY APPLICATION

This application is based upon and claims the benefit under 35 U.S.C. § 119(e) of U.S. Provisional Patent Application Ser. No. 61/759,774, filed Feb. 1, 2013, which is incorporated herein by reference in its entirety for all purposes.

CROSS-REFERENCE TO OTHER MATERIALS

This application incorporates by reference in their entireties for all purposes the following patent documents: U.S. Pat. No. 7,041,481, issued May 9, 2006; U.S. Patent Pub. No. US-2010-0173394-A1; and U.S. Patent Pub. No. 2011-0311978-A1.

INTRODUCTION

Many biomedical applications rely on high-throughput assays of samples combined with reagents. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

The trend is toward reduced volumes and detection of more targets. However, creating and mixing smaller volumes can require more complex instrumentation, which increases cost. Accordingly, improved technology is needed to permit testing greater numbers of samples and combinations of samples and reagents, at a higher speed, a lower cost, and/or with reduced instrument complexity.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (picoliters to nanoliters) can be utilized, allowing earlier detection by increasing reaction rates and forming more concentrated products. Also, a much greater number of independent measurements (thousands to millions) can be made on the sample, when compared to conventional bulk volume reactions performed on a micoliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for the generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nuclei acid target molecules in droplets using the polymerase chain reaction (PCR).

Compartmentalization of single molecules of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

Despite their allure, emulsion-based assays present technical challenges for high-throughput testing. As an example, the arrangement and packing density of droplets may need to be changed during an assay, such as after the droplets have been reacted and before detection. In particular, it may be advantageous to thermally cycle droplets at a high packing density in a batch mode. However, detection of signals from closely packed droplets may be problematic because the signals cannot always be correctly assigned to individual droplets. Thus, there is a need for systems that space droplets from one another after reaction and before detection for improved detection accuracy.

SUMMARY

The present disclosure provides a system, including methods and apparatus, for spacing droplets (or other particles of interest) from each other and for detection of spaced droplets.

BRIEF DESCRIPTION OF THE DRAWINGS

FIG. 14 depicts a sectional view of an alternative droplet singulator that may be used in conjunction with a detection system for droplet-based assays, in accordance with aspects of the present disclosure.

FIG. 16 is a flow chart depicting a method of detecting fluorescence from sample-containing droplets, in accordance with aspects of the present disclosure.

DETAILED DESCRIPTION

Figure 1:
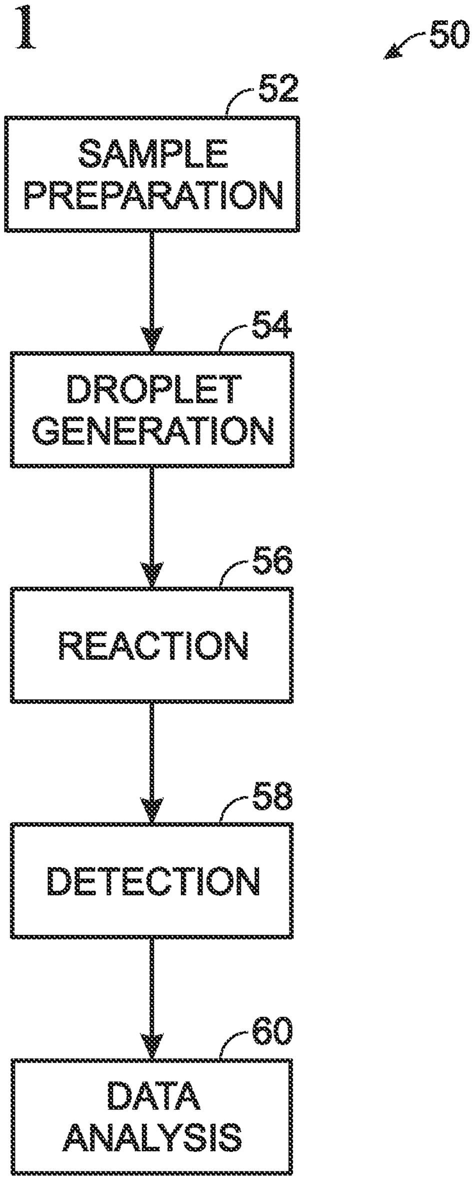
FIG. 1 is a flowchart listing exemplary steps that may be performed in a method of sample analysis using droplets and droplet-based assays, in accordance with aspects of the present disclosure.

The present disclosure provides a system, including methods and apparatus, for spacing droplets from each other and for detection of spaced droplets. The system particularly involves a droplet spacer that increases the average distance between droplets, and that optionally arranges droplets in single file in a flow stream that is upstream of an examination region in a flow path, to permit serial detection of individual, spaced droplets passing through the examination region.

The system disclosed herein, while generally described in the context of droplets, may in many cases be used with particles in general. A particle generally comprises any object that is small enough to be inputted and manipulated within a microfluidic network in association with fluid, but that is large enough to be distinguishable from the fluid. Particles, as used here, typically are microscopic or near-microscopic, and may have diameters of about 0.005 to 100 μm, 0.1 to 50 μm, or about 0.5 to 30 μm, among others. In the case of droplets, the particles may be described as being on the order of a nanoliter. In addition to the droplets described herein, illustrative particles may include cells, viruses, organelles, beads, and/or vesicles, and aggregates thereof, such as dimers, trimers, etc. Except where the context clearly indicates otherwise, the terms droplet and particle, as used herein, may be interchangeable.

A system for spacing droplets and/or particles from each other, also interchangeably referred to as a droplet singulator or droplet spacer, is provided. The system may comprise a channel network including a droplet channel through which droplets of sample fluid suspended in a carrier fluid are configured to pass. The system also may comprise a shell surrounding a portion of the droplet channel, including a plurality of dilution channels formed within the shell and configured to transport dilution fluid to the droplet channel at a controlled rate or rates, resulting in a desired amount of spacing between droplets traveling through the droplet channel.

A detection system for droplet-based assays is provided. In addition to the elements of a droplet singulator, a detection system also may comprise a detector operatively connected to the channel network and configured to detect radiation, such as fluorescence radiation, emitted by the spaced-apart droplets in an examination or detection region downstream from the portion of the channel network within which the dilution fluid is transported into the droplet channel.

A method for detecting radiation emitted by droplets in a droplet-based assay is provided. The method may comprise inputting droplets of a sample fluid suspended in a carrier fluid into a droplet channel, transporting the droplets downstream through the droplet channel to a dilution region, transporting dilution fluid into a shell surrounding the droplet channel in the dilution region, transporting the dilution fluid from the shell into the droplet channel to achieve a desired spacing between droplets, transporting the spaced-apart droplets to a detection region, and detecting fluorescence or other radiation emitted by droplets passing through the detection region.

FIG. 1 shows an exemplary system 50 for performing a droplet- or partition-based assay. In brief, the system may include sample preparation 52, droplet generation 54, reaction 56 (e.g., amplification), detection 58, and data analysis 60. In some examples, the system may be utilized to perform a digital PCR (polymerase chain reaction) analysis.

More specifically, sample preparation 52 may involve collecting a sample, such as a clinical or environmental sample, treating the sample to release an analyte (e.g., a nucleic acid or protein, among others), and forming a reaction mixture involving the analyte (e.g., for amplification of a target nucleic acid that corresponds to the analyte or that is generated in a reaction (e.g., a ligation reaction) dependent on the analyte). Droplet generation 54 may involve encapsulating the analyte and/or target nucleic acid in droplets, for example, with an average of about one copy of each analyte and/or target nucleic acid per droplet, where the droplets are suspended in an immiscible carrier fluid, such as oil, to form an emulsion. Reaction 56 may involve subjecting the droplets to a suitable reaction, such as thermal cycling to induce PCR amplification, so that target nucleic acids, if any, within the droplets are amplified to form additional copies. Detection 58 may involve detecting some signal(s) from the droplets indicative of whether or not amplification was successful. Finally, data analysis 60 may involve estimating a concentration of the analyte and/or target nucleic acid in the sample based on the percentage of droplets in which amplification occurred.

These and other aspects of the system are described in further detail below, particularly with respect to exemplary detection systems and/or droplet spacers, and in the patent documents listed above under Cross-References and incorporated herein by reference.

I. Detection System Overview

The present disclosure describes exemplary detection systems, for example, for detecting sample-containing droplets. The systems may involve sensing or detecting the droplets themselves and/or contents of the droplets. The detection of droplets themselves may include determining the presence or absence of a droplet (or a plurality of droplets) and/or a characteristic(s) of the droplet, such as its size (e.g., radius or volume), shape, type, and/or aggregation state, among others. The detection of the contents of droplets may include determining the nature of the contents (e.g., whether or not the droplet contains a sample(s)) and/or a characteristic of the contents (e.g., whether or not the contents have undergone a reaction, such as PCR, the extent of any such reaction, etc.).

The detection of droplets and their contents, if both are detected, may be performed independently or coordinately, in any suitable order. For example, the detection may be performed serially (one droplet at a time), in parallel, in batch, and so forth.

The detection of droplets and their contents may be performed using any technique(s) or mechanism(s) capable of yielding, or being processed to yield, the desired information. These mechanisms may include optical techniques (e.g., absorbance, transmission, reflection, scattering, birefringence, dichroism, fluorescence, phosphorescence, etc.), electrical techniques (e.g., capacitance), and/or acoustic techniques (e.g., ultrasound), among others. The fluorescence techniques, in turn, may include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

The present disclosure describes exemplary detection systems, including droplet sensors and reaction sensors. In these exemplary systems, the droplet sensor may generate and detect scattered light, and the reaction sensor may generate and detect fluorescence, among other approaches. These systems are described, for convenience, in the context of a PCR reaction; however, the techniques apply more generally to any reaction, such as a biochemical reaction, capable of generating, or being modified to generate, a detectable signal.

In an exemplary PCR assay (or other nucleic acid amplification assay), the sample is first combined with reagents in a droplet, and the droplet is then thermocycled to induce PCR. It may then be desirable to measure the fluorescence of the droplets to determine which, if any, contained one or more target nucleotide sequences. This generally involves illuminating the droplets with radiation at a wavelength chosen to induce fluorescence, or a change in a characteristic of the fluorescence, from one or more fluorescent probes associated with the amplified PCR target sequence(s). For example, in an exemplary fluorescence intensity assay, if a relatively large intensity of fluorescence is detected, this indicates that PCR amplification of the target nucleotide occurred in the droplet, and thus that the target was present in that portion of the sample. Conversely, if no fluorescence or a relatively small intensity of fluorescence is detected, this indicates that PCR amplification of the target nucleotide did not occur in the droplet, and thus that a target was likely not present in that portion of the sample. In other fluorescence-based embodiments, the extent of reaction could be determined from a decrease in fluorescence intensity, instead of a decrease, and/or a change in one or more other fluorescence parameters, including polarization, energy transfer, and/or lifetime, among others.

II. Droplet Spacer Overview

The present disclosure describes exemplary droplet spacers, also termed droplet singulators, spacers, or separators, that may be positioned in a flow path of a detection system and/or droplet transport system. A spacer may be disposed at any suitable position, such as in fluid communication with and upstream of a detection or examination region (e.g., an irradiation zone), in fluid communication with and downstream of an incubation/reaction site (e.g., a thermal cycling region), or both, among others. The spacer may increase or decrease the average distance between droplets in a flow stream, may cause the droplets to transition from a multiple file or bulk arrangement to a single file arrangement, and/or may focus droplets within the flow stream.

The droplet spacer may include at least two inlet channels, an outlet channel, and a dilution region or separation region forming a junction between the inlet channels and the outlet channel. The at least two inlet channels may include a droplet inlet channel that receives an emulsion of droplets dispersed in a continuous phase, and at least one carrier or dilution channel that receives a dilution fluid, such as an oil, for diluting the droplets/emulsion. The dilution fluid received in the dilution channel may be the same as, or different from, the carrier fluid in which the droplets are disposed in the droplet inlet channel.

The droplet spacer may include any suitable configuration, layout, or arrangement configured to place the inlet channels and outlet channel into fluid communication. For example, the inlet channels and the outlet channel collectively may form a T, a cross, a coaxial arrangement, or the like.

The droplet inlet channel may have a uniform diameter or may taper toward the dilution region. If tapered, the droplet inlet channel may have a maximum diameter that is greater than that of the droplets (e.g., at least about 50%, 100%, 150%, 200%, or 300% greater in diameter, among others). The droplet inlet channel may taper to a minimum diameter (e.g., adjacent the dilution region) that is about the same or less than the diameter of the droplets. For example, the diameter of the droplet inlet channel may be between about 90% and about 100% of an average diameter of the droplets, among others. The use of a minimum diameter that is about the same or less than the diameter of the droplets may permit only one droplet to enter the dilution region at a time, thereby facilitating production of a single-file stream of droplets for a downstream detection site. While the resulting droplet arrangement may be single-file, however, the droplets may not yet be spaced sufficiently for the detection system to distinguish one droplet from another.

The dilution channel (or channels) may have a diameter that is less than, about the same as, or greater than the maximum or minimum diameter of the droplet inlet channel. The droplet spacer may have any suitable number of dilution channels, such as one, two, three, or more. The dilution channel(s) thus may be disposed on only side of the dilution region, on opposing sides, on three or more sides, etc. In some examples, the dilution channels may communicate with the dilution region circumferentially, i.e., from several or all sides of a surrounding circumferential housing or shell.

The dilution region may include any suitable structure configured to dilute the droplet stream. The dilution region may include a portion of the droplet channel having a diameter that is greater than the minimum diameter of the droplet inlet channel and greater than the diameter of the droplets. As a result, any droplets newly-formed at the droplet spacer (such as by fragmentation of a coalesced set of droplets) should be larger than the original droplets of interest. Accordingly, any droplets detected to be larger than a threshold size by a downstream detector (and thus likely to be formed after thermal cycling) may be excluded from the analysis. The dilution region may taper from a larger diameter to a smaller diameter toward the outlet channel, which may act to accelerate each individual droplet out of the dilution region. Furthermore, in some cases the droplet inlet channel and the droplet outlet channel may be near one another, such as separated by no more than about twice, once, or one-half the droplet diameter, to promote exit of droplets from the dilution region, thereby allowing only one droplet to be present in the dilution region at a time.

The droplet spacer may define a minimum diameter along a flow path followed by droplets between a pick-up tip and an examination region. Accordingly, the spacer may provide a maximum resistance to fluid flow along the flow path. Fluid may be driven along the flow path at a sufficient velocity to provide a high shear, to help prevent clogs and remove particulates. The high shear also may help to increase the distance between droplets.

Further aspects of transport systems/detection systems involving droplet spacers are described below.

III. Examples

The following examples describe specific exemplary detection systems and spacers, in accordance with aspects of the invention. Additional pertinent disclosure may be found in the patent documents listed above under Cross-References and incorporated herein by reference, particularly Ser. No. 61/277,203, filed Sep. 21, 2009; U.S. Provisional Patent Application Ser. No. 61/317,635, filed Mar. 25, 2010; U.S. Provisional Patent Application Ser. No. 61/467,347, filed Mar. 24, 2011; and U.S. patent application Ser. No. 12/586,626, filed Sep. 23, 2009, Pub. No. US-2010-0173394-A1.

Example 1

Detection System 1

This example describes an optical detection system based on measuring the end-point fluorescence signal of each sample/reagent droplet after a PCR amplification process is complete. The exemplary system is suitable for making both qualitative and quantitative measurements; see FIGS. 2 and 3.

Figure 2:
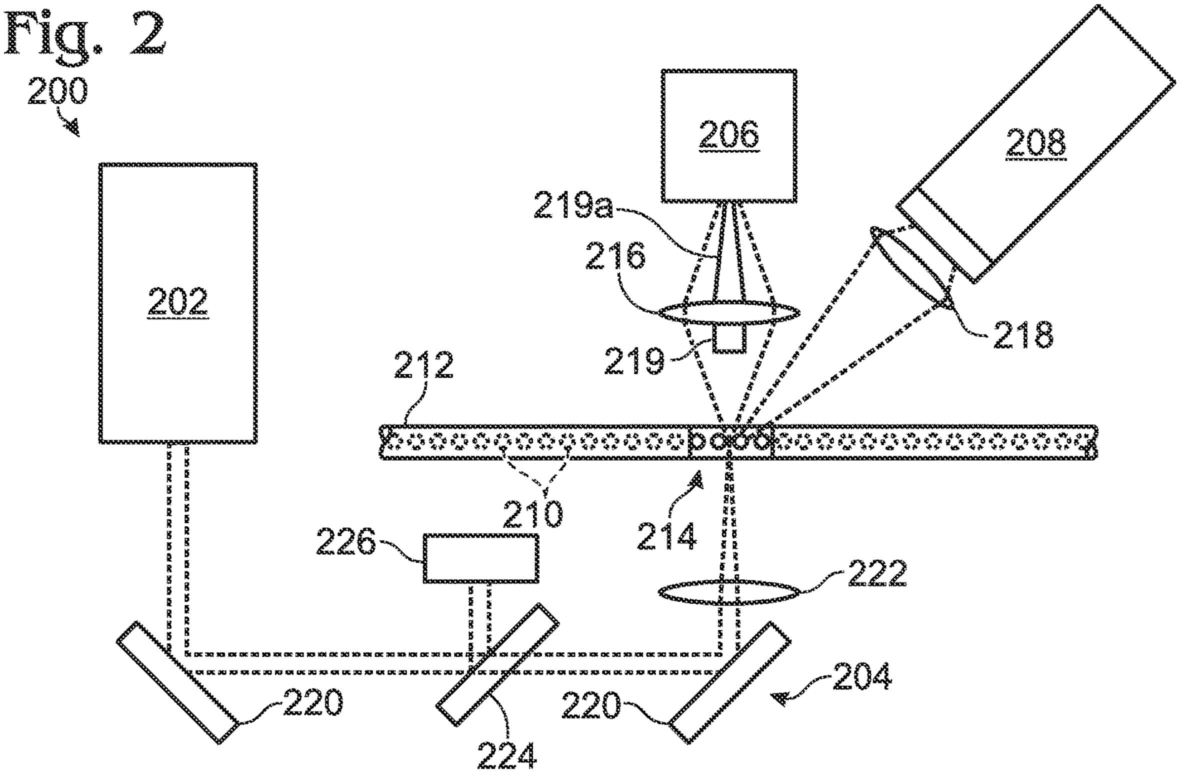
FIG. 2 is a schematic depiction of an optical detection system for irradiating sample-containing droplets and detecting fluorescence subsequently emitted by the droplets, in accordance with aspects of the present disclosure.

FIG. 2 depicts a detection system 200 configured to detect both scattered and fluorescence radiation. Detection system 200 includes a radiation source 202, transmission optics generally indicated at 204, a forward scatter detector 206, and a fluorescence detector 208. The forward scatter detector may be replaced or augmented, in some embodiments, by side and/or back scatter detectors, among others, configured to detect light scattered to the side or back of the sample, respectively. Similarly, the fluorescence detector may be replaced or augmented, in some embodiments, by an epi-fluorescence detector, among others, configured to detect fluorescence emitted anti-parallel to the excitation light (e.g., back toward transmission optics 204 (which could, in such embodiments, include a dichroic or multi-dichroic beam splitter and suitable excitation and emission filters)).

Sample-containing droplets 210, which have already undergone at least some degree of PCR thermocycling, are transferred through a capillary tube or other similar fluid channel 212, which intersects the path of radiation from radiation source 202 at an intersection region generally indicated at 214. An optical element 216, such as a converging lens, may be placed between intersection region 214 and forward scatter detector 206, to focus scattered radiation on the scatter detector. Similarly, an optical element 218 may be placed between intersection region 214 and fluorescence detector 208, to focus fluorescence radiation on the fluorescence detector. The system may include an obscuration bar 219, operatively positioned between the sample and detector, which reduces the amount of direct (unscattered) excitation radiation (light) that falls on the detector. The obscuration bar, shown here as a small square object in front of optical element 216, may create a triangular-shaped shadow 219*a* behind the optical element. This arrangement makes it easier for detector 206 to detect changes in index of refraction that have scattered (at small angles) the normal beam.

Radiation from source 202 may be partially scattered because it encounters a droplet, and the scattered radiation may be used to determine one or more properties of the droplet. For example, scattered radiation indicating the presence of a droplet in intersection region 214 may be sensed by scatter detector 206, and this information may be used to activate fluorescence detector 208, which may otherwise remain deactivated (i.e., when a droplet is not present in the intersection region) to conserve power within the system. Even if the fluorescence detector remains continuously active, detecting the presence of a droplet may be useful for other purposes. For example, tracking the droplets passing through intersection region 214 may be desirable because some droplets passing through the intersection region may not be detected by the fluorescence detector (e.g., if the droplets do not contain reaction product). In addition, tracking the droplets may allow background noise (i.e., the signal received by the detector in the absence of a droplet) to be removed, improving the signal-to-noise ratio.

Furthermore, as described below, various properties of a detected droplet may be estimated from data sensed by forward or side scatter detector 206.

Radiation detected by scatter detector 206 may be used to infer the size (or other properties) of a detected droplet. Specifically, a measurement of the duration of a scattering event representing the presence of a droplet within intersection region 214, in conjunction with knowledge of the average speed of droplet passage through the intersection region, can be used to determine the width of the droplet in a plane normal to the direction of the incident radiation from source 202. If this width is less than the diameter of channel 214, then it can be inferred that the droplet is an approximate sphere with a diameter less than the diameter of channel 214, and the volume of the droplet can be calculated. If, on the other hand, the width of the droplet exceeds the diameter of channel 214, this indicates that the droplet is likely contacting the walls of the channel and is not spherical. However, the droplet volume still may be estimated by modeling the droplet as a cylinder or other similar shape passing through the channel. As described below, a determination of droplet volume may be useful for normalizing the results of any corresponding fluorescence detection.

In some cases, radiation from source 202 also may be scattered from intersection region 214 even if it does not encounter a droplet, for instance, if it encounters a partially reflective surface such as a fluid interface or a wall of fluid channel 212. This type of scattered radiation will generally have a different signature than radiation scattered from a droplet, so that it generally serves merely as a background for droplet scattering events. Whether scattering occurs in the absence of a droplet depends on the particular configuration of system 200, as will be described below. Similarly, scattering may occur when droplets outside a desired size range pass through the intersection region, and the signature of radiation scattered from such droplets may be used to affect the subsequent treatment of such droplets. For example, the fluorescence signals received from unusually small or large droplets may be removed from a statistical sample, to increase statistical accuracy. In any case, after passing through intersection region 214, scattered and/or unscattered radiation from radiation source 202 is directed toward forward scatter detector 206.

Radiation from source 202 that is absorbed by droplets within intersection region 214 may stimulate the emission of fluorescence radiation that can be detected by fluorescence detector 208. More specifically, radiation intersecting a droplet may excite a fluorescent probe, such as a TAQMAN probe, that is configured to fluoresce significantly only if the fluorescent portion of the probe becomes separated from a quencher molecule. This separation, or cleaving, typically occurs only when polymerase replicates a sequence to which the probe is bound. In other words, a probe will fluoresce significantly only in droplets within which a target nucleotide sequence has been amplified through PCR. Accordingly, radiation source 202 will generally be configured to emit radiation at a wavelength that stimulates fluorescence emission from one or more probes known to be present in the sample, and fluorescence detector 208 will be configured to detect such stimulated radiation.

Radiation source 202 may take any form suitable for transmitting radiation at one or more desired wavelengths or wavelength bands. For example, radiation source 202 may be a laser, such as a diode laser, emitting substantially monochromatic light at a wavelength of 488 nanometers (nm) or at some other desired wavelength. Radiation source 202 also may include multiple separate lasers, emitting light at either a single wavelength or at multiple different wavelengths. One or more (or all) of the lasers of radiation source 202 may be replaced by an alternate source of light, such as a light-emitting diode (LED) configured to emit a directed beam of radiation at one or more desired wavelengths. In yet other embodiments, white light illumination, for example, from a Halogen lamp, may also be used to provide the radiation source.

Transmission optics 204 may include any optical components suitable for directing, focusing, or otherwise desirably affecting radiation from source 202. For example, as depicted in FIG. 2, the transmission optics may include one or more steering mirrors 220, each configured to direct incident radiation in a desired direction such as toward another optical component or toward intersection region 214. Also as depicted in FIG. 2, the transmission optics may include a converging lens 222, which is configured to focus radiation from source 202 onto intersection region 214 to maximize scattering and fluorescence caused by the radiation. The transmission optics may further include additional components such as aperture stops, filters, diverging lenses, shaped mirrors, and the like, to affect the transmission path and/or properties of the radiation from source 202 before it arrives at intersection region 214. In addition, the transmission optics further may include (in this and other embodiments) a mechanism for monitoring properties of the incident (excitation) radiation. For example, the transmission optics may include a partial mirror 224 for reflecting a portion of the incident radiation to a detector 226, such as a photodiode, for monitoring the intensity of the incident light. This would allow correction of the detected scattering and fluorescence for changes that simply reflect changes in the intensity of the incident light.

Forward scatter detector 206 is configured to receive and detect radiation scattered from droplets passing through intersection region 214, as described previously. Various types of detectors may be suitable, depending on the desired cost and/or sensitivity of the detector. In approximate order of decreasing sensitivity, exemplary types of scatter detectors that may be suitable include photodiodes, avalanche photodiodes, multi-pixel photon counters, and photomultiplier tubes. The presence of optical element 216, which typically will be a converging lens used to refocus scattered radiation toward scatter detector 206, may decrease the necessary sensitivity of the forward scatter detector for a given application, by increasing the intensity per unit area of scattered radiation incident on the detector.

Fluorescence detector 208 is configured to receive and detect fluorescence radiation emitted by droplets at or near the time they pass through intersection region 214. Various types of fluorescence detectors may be suitable, depending on factors such as desired cost and/or sensitivity, including photodiodes, avalanche photodiodes, multi-pixel photon counters, and photomultiplier tubes. Also as in the case of the forward scatter, utilizing an optical element 218, typically a converging lens, between intersection region 214 and fluorescence detector 208 may decrease the necessary sensitivity of the fluorescence detector by increasing the intensity per unit area of fluorescence radiation incident on the detector.

Figure 3:
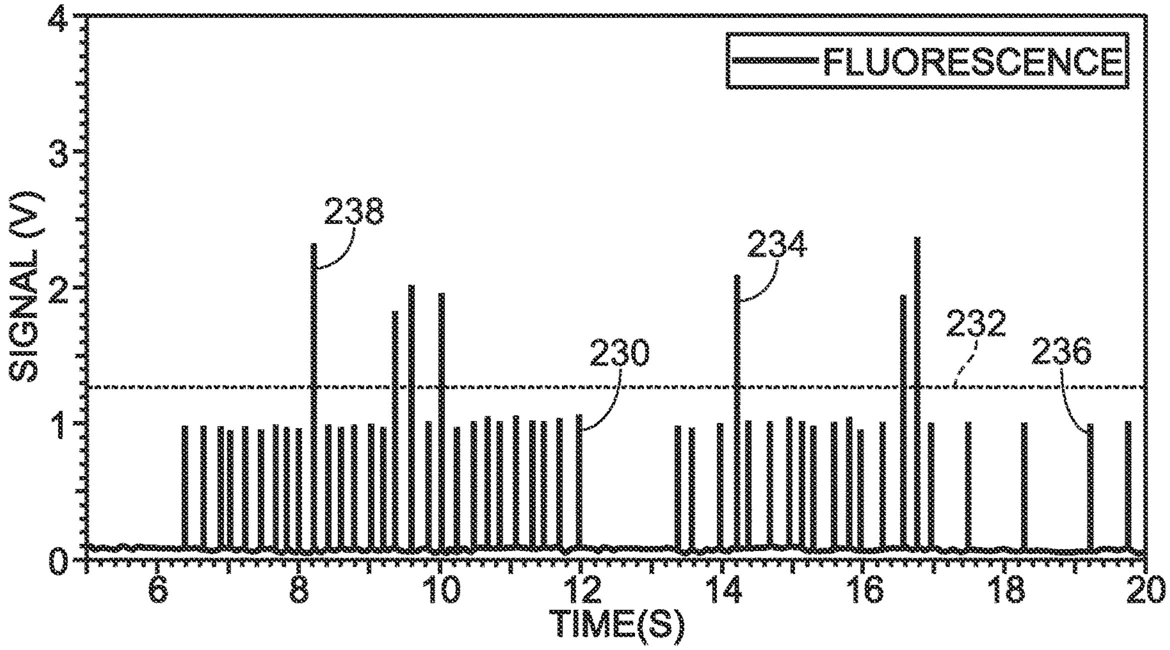
FIG. 3 is a graph of intensity versus time for fluorescence detected by an optical detection system such as the system of FIG. 2, illustrating the distinction between fluorescence emitted by droplets containing a target and droplets not containing a target.

FIG. 3 depicts exemplary fluorescence measurements made by fluorescence detector 208. More specifically, FIG. 3 shows a post-PCR end-point fluorescence trace from droplets, in which each "peak" 230 represents the intensity of detected fluorescence emitted by an individual droplet flowing through intersection region 214. As FIG. 3 indicates, the resulting histogram can be used to identify positive from negative signals. Specifically, the signals depicted in FIG. 3 each may be compared to a cut-off or threshold fluorescence level, as indicated by dashed line 232. Signals exceeding the threshold level will be interpreted as positive for PCR amplification, and thus for the presence of the target nucleotide sequence in the corresponding droplet, as indicated for an exemplary signal at 234. On the other hand, signals falling below threshold level 232 will be interpreted as negative outcomes, indicating that the corresponding droplet did not contain the target.

An example of a negative signal is indicated at 236, where the detection of a sub-threshold amount of fluorescence is due to the presence of uncleaved fluorescent probe in the droplet. As described previously, the fluorescence of such probes is generally not completely quenched even in the absence of cleavage by a binding polymerase. Also, the differences in fluorescence intensity of a positive, as seen in the signal voltage peak heights between the positive peak at 238 and positive peak 234, can be attributed to different amounts of starting nucleic acid target originally in the droplet prior to PCR (e.g., one versus two starting targets). The ratio of different amounts of starting target amounts may be governed by Poisson statistics.

Typically, hundreds to millions of droplets are analyzed per run. In any case, after a desired number of signals have been detected by fluorescence detector 208, i.e., after a desired number of droplets have passed through intersection region 214, the positive and negative signals are counted and analyzed. Analysis is typically performed using receiver-operator characteristic curves and Poisson statistics to determine target presence and target concentration, respectively. Running analysis using Poisson statistics can also be performed to give an estimate of target concentration prior to processing all the droplets (i.e., subsets of the total droplets are used in the statistical analysis). The analysis of droplets is further described in U.S. patent application Ser. No. 12/586,626, filed Sep. 23, 2009, Pub. No. US-2010-0173394-A1, which is incorporated herein by reference.

Example 2

Detection Systems Using Optical Fibers

This example describes fluorescence detectors configured to measure the end-point fluorescence signal of sample/reagent droplet after PCR, and which utilize one or more optical fibers to transmit radiation to and/or from an intersection region within which illuminating radiation intersects the path of the sample-containing droplets. The exemplary systems are suitable for making both qualitative and quantitative measurements; see FIGS. 4-9.

Figure 4:
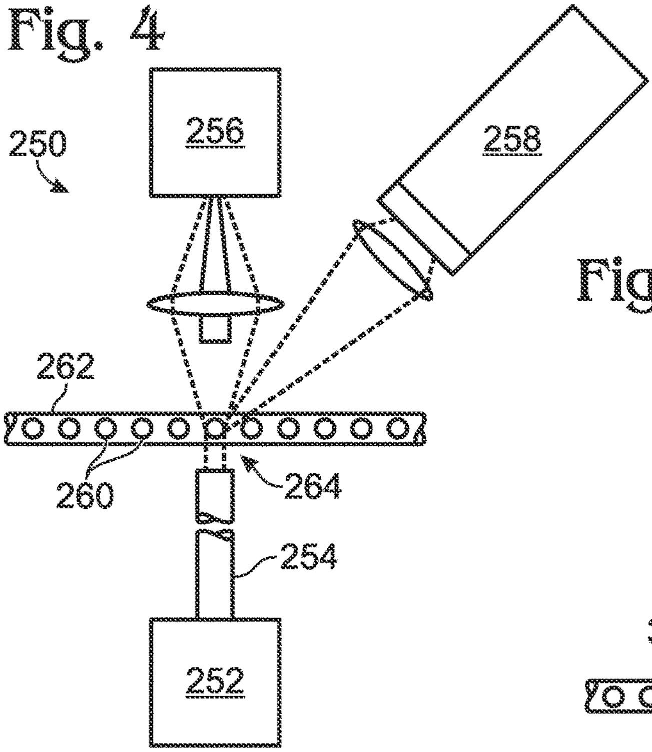
FIG. 4 is a schematic depiction of an optical detection system in which stimulating radiation is transferred toward sample-containing droplets through an optical fiber, in accordance with aspects of the present disclosure.

FIG. 4 depicts an optical detection system, generally indicated at 250, which is similar to system 200 depicted in FIG. 2 except that transmission optics 204 of system 200 have been replaced by an optical fiber 254. Optical fiber 254 may be constructed from a glass, a plastic, and/or any other material that is substantially transparent to radiation of one or more particular desired wavelengths and configured to transmit that radiation along the length of the fiber, preferably with little or no loss of intensity.

Replacing the transmission optics with optical fiber 254 may allow system 250 to be constructed relatively inexpensively and in a more space-saving manner than systems using optical elements such as mirrors and lenses. This results from the fact that the cost and space associated with the other optical elements is no longer necessary, and also from the fact that optical fiber 254 may be shaped in any desired manner, allowing significant design flexibility. Aside from optical fiber 254, detection system 250 otherwise includes a radiation source 252, a forward scatter detector 256, and a fluorescence detector 258, all of which are similar to their counterparts in system 200 and will not be described again in detail.

Optical fiber 254 is depicted in FIG. 4 as ending a short distance from droplets 260 traveling in fluid channel 262 through an intersection region generally indicated at 264, in which radiation emitted from the end of the optical fiber intersects with the droplets traveling through the fluid channel. Other configurations are possible in which, for example, the optical fiber is configured to focus radiation more precisely toward the intersection region and/or is integrated directly into the fluid channel. These possibilities are described below in more detail; see FIGS. 7-9 and accompanying discussion.

Figure 5:
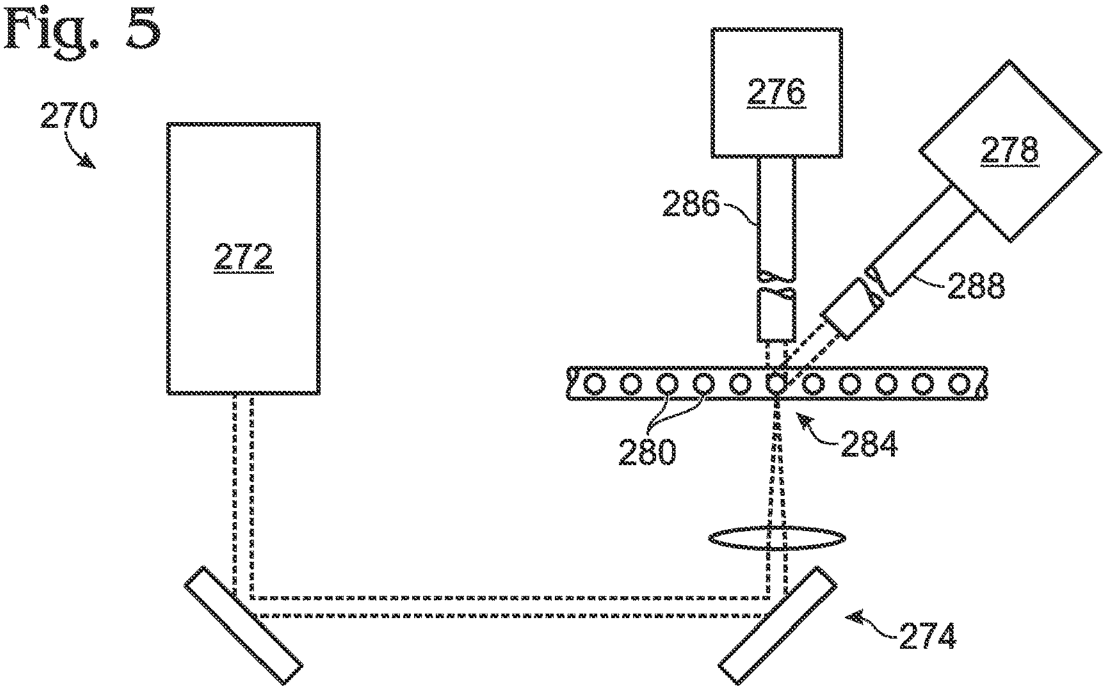
FIG. 5 is a schematic depiction of an optical detection system in which scattered and fluorescence radiation are transferred away from sample-containing droplets through optical fibers, in accordance with aspects of the present disclosure.

FIG. 5 depicts an optical detection system, generally indicated at 270, which is similar to system 200 depicted in FIG. 2 except that optical elements 216 and 218 of system 200 have been replaced by optical fibers 286 and 288 in system 270 of FIG. 5. As in the case of optical fiber 254 shown in FIG. 4 and described above, optical fibers 286 and 288 each may be constructed from a glass, a plastic, and/or any other material that is substantially transparent to radiation of one or more particular desired wavelengths and configured to transmit that radiation along the length of the fiber, preferably with little or no loss of intensity.

In the case of system 270, optical fiber 286 will be configured to transmit at least scattered radiation having a wavelength equal to the wavelength of light emitted by radiation source 272 (which generally does not change during scattering), and optical fiber 288 will be configured to transmit at least fluorescence radiation emitted by any fluorescent probes within droplets 280 that are excited by incident radiation from source 272. Accordingly, optical fibers 286 and 288 may in some cases be constructed from different materials. The use of optical fibers 286 and 288 may result in cost and space savings for the same reasons described previously with respect to the use of optical fiber 254 in system 250.

Aside from the use of optical fibers 286 and 288, system 270 is similar to system 200, including radiation source 272, transmission optics 274, a forward scatter detector 276, and a fluorescence detector 278, which are similar to their previously described counterparts and will not be described further. Radiation from source 272 passes through transmission optics 274 and encounters droplets 280 traveling through fluid channel 282, at an intersection region 284. Some of the forward scattered radiation is transmitted through optical fiber 286 to forward scatter detector 276. Similarly, some of the fluorescence radiation emitted from droplets 280 is transmitted through optical fiber 288 to fluorescence detector 278. As in the case of optical fiber 254 in FIG. 4, optical fibers 286 and 288 are shown starting at a distance from fluid channel 282, but as noted above, other configurations are possible and will be described below with reference to FIGS. 7-9.

Figure 6:
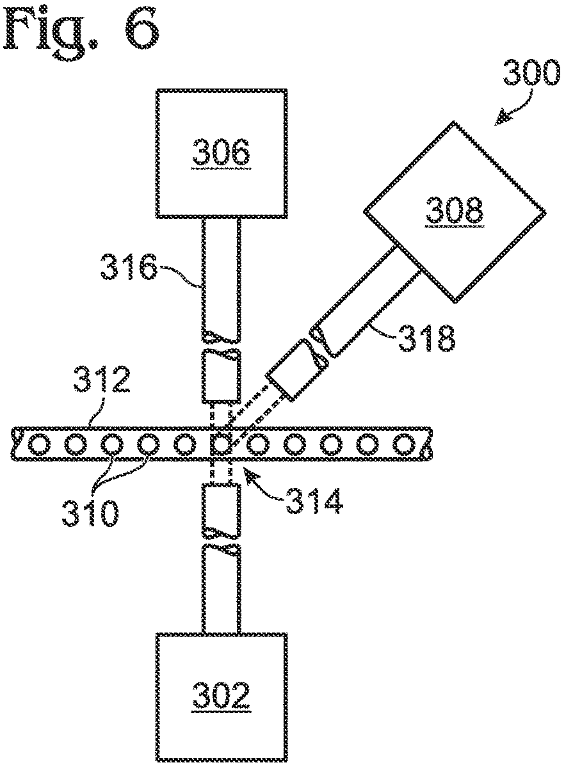
FIG. 6 is a schematic depiction of an optical detection system in which stimulating radiation is transferred toward sample-containing droplets through an optical fiber and in which scattered and fluorescence radiation are transferred away from the droplets through optical fibers, in accordance with aspects of the present disclosure.

FIG. 6 depicts an optical detection system, generally indicated at 300, in which optical fibers are used to transmit both incident and outgoing radiation. More specifically, system 300 includes a radiation source 302, an optical fiber 304 for transmitting emitted radiation away from source 302, a forward scatter detector 306, and a fluorescence detector 308. Post-PCR sample-containing droplets 310 are transferred through fluid channel 312 toward intersection region 314. Optical fiber 316 transmits scattered radiation from intersection region 314 to forward scatter detector 306, and optical fiber 318 transmits fluorescence radiation from intersection region 314 to fluorescence detector 308.

As described previously, the use of optical fibers may result in various cost and space savings. These savings may be further amplified, relative to systems 250 and 270, by the use of fiber optics for all of the radiation transfer in system 300. Aside from the use of optical fibers for radiation transfer and any associated efficiencies, system 300 is similar in both its components and its operation to the previously described systems, and accordingly will not be described further.

Figure 7:
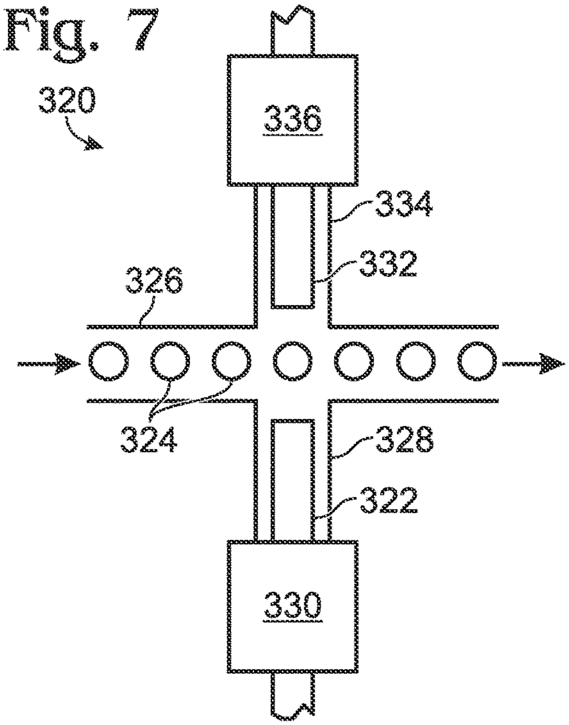
FIG. 7 depicts an intersection region where incident radiation intersects with sample-containing droplets traveling through a fluid channel, illustrating how optical fibers may be integrated with sections of fluidic tubing.

FIG. 7 shows a magnified view of an intersection region, generally indicated at 320, in which incident radiation from a radiation source (not shown) is transmitted through an optical fiber 322 to intersect with sample-containing droplets 324 traveling through a droplet input fluid channel 326. Intersection region 320 differs from the intersection regions described previously in that optical fiber 322 is integrated into a radiation input fluid channel 328 that is fluidically connected with fluid channel 326. Thus, radiation is emitted from optical fiber 322 directly into the fluid within the connected fluid channels, so that it encounters droplets 324 without crossing either an interface between air and the fluid channel material (typically some form of glass) or an interface between the fluid channel material and the fluid within the channel.

By configuring the intersection region in this manner and avoiding two interfaces between media with different indices of refraction, undesirable reflections of the incident radiation may be decreased, resulting in a greater intensity of radiation reaching droplets 324. Furthermore, embedding optical fiber 322 within a connected fluid channel may allow for more convenient and stable placement of the optical fiber at a small distance from fluid channel 326 and at a desired orientation relative to fluid channel 326, again potentially resulting in a greater intensity of radiation reaching the droplets. To secure optical fiber 322 in place within channel 328, a fluidic fitting 330 may be placed at an end of channel 328, and configured so that optical fiber 322 passes through an aperture of the fitting in a fluid tight manner.

Intersection regions of the type depicted in FIG. 7 may take various forms. For example, as depicted in FIG. 7, optical fiber 322 may have a slightly smaller outer diameter than the inner diameter of fluid channel 328. Alternatively, optical fiber 322 may have an outer diameter approximately equal to the inner diameter of fluid channel 328, which may lead to an even more secure placement of the optical fiber within the fluid channel. In addition, FIG. 7 depicts an outgoing optical fiber 332 disposed within a fluid channel 334 that is also fluidically connected with fluid channel 326. Optical fiber 332, which is secured within channel 334 by a fluidic fitting 336, is configured to transmit scattered radiation to a forward scatter detector (not shown). In some embodiments, one of incoming optical fiber 322 and outgoing optical fiber 332 may be used, but not the other. Furthermore, one or more additional optical fibers, such as an outgoing optical fiber leading to a fluorescence detector (not shown) may be fluidically coupled into intersection region 320.

Figure 8:
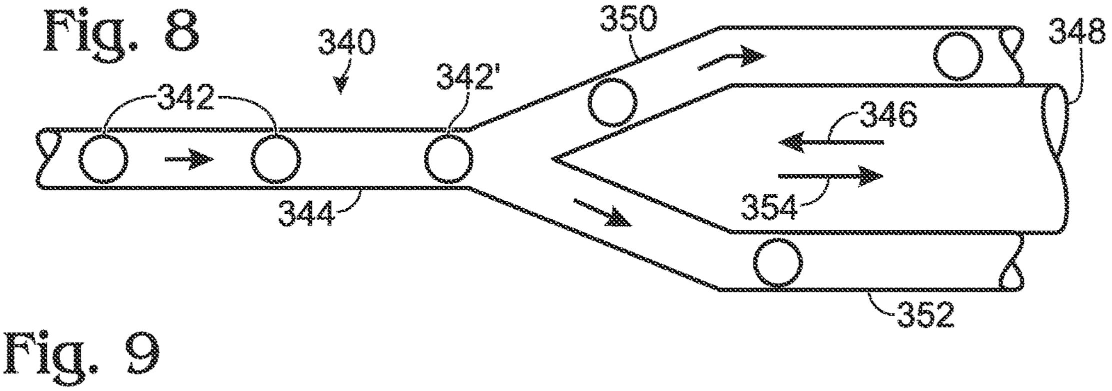
FIG. 8 depicts another intersection region where incident radiation intersects with sample-containing droplets traveling through a fluid channel, illustrating how a single optical fiber may be used to transmit both incident radiation and stimulated fluorescence.

FIG. 8 depicts another intersection region, generally indicated at 340, between sample-containing droplets 342 traveling through a fluid channel 344 and excitation radiation 346 emitted from a radiation source (not shown). Excitation radiation 346 is transmitted to intersection region 340 through an optical fiber 348, which is oriented with its long axis parallel to fluid channel 344. As depicted in FIG. 8, optical fiber 348 may come to a point or otherwise be tapered in the region proximal to fluid channel 344, to focus excitation radiation 346 (through internal reflections within the optical fiber) into channel 344 and toward droplets 342. This may allow the excitation radiation to be directed primarily at a single droplet 342', despite the collinear disposition of optical fiber 348 with multiple droplets.

Fluid channel 344, which is configured to transport the droplets to intersection region 340 where the droplets encounter stimulating radiation transmitted by optical fiber 348, is shown splitting into two (or more) outgoing fluid channels 350 and 352 after droplets 342 pass through the central part of intersection region 340. This allows the sample-containing droplets to continue their motion through the PCR system while still allowing a collinear arrangement of fluid channel 344 and optical fiber 348. As FIG. 8 illustrates, the outgoing fluid channels and the optical fiber may be given complementary shapes, so that the optical fiber fits snugly between outgoing channels 350 and 352. This may lead to a relatively stable collinear configuration of the optical fiber and fluid channel 344 (to help self-align the fiber and channel).

The intersection region shown in FIG. 8 is configured so that optical fiber 348 transmits both excitation radiation 346 and also fluorescence radiation 354 emitted by the droplets. The fluorescence radiation is then transmitted back through the optical fiber and toward a fluorescence detector (not shown), which may be integrated with a radiation source into a single component. Due to the shape of the proximal end of optical fiber 348, emitted fluorescence radiation from stimulated droplet 342' may enter optical fiber 348 both "head on" and also from a subsequent position along one side of the optical fiber. This effectively lengthens the integration time of the fluorescence detection, resulting in better detection with a given detector sensitivity.

Figure 9:
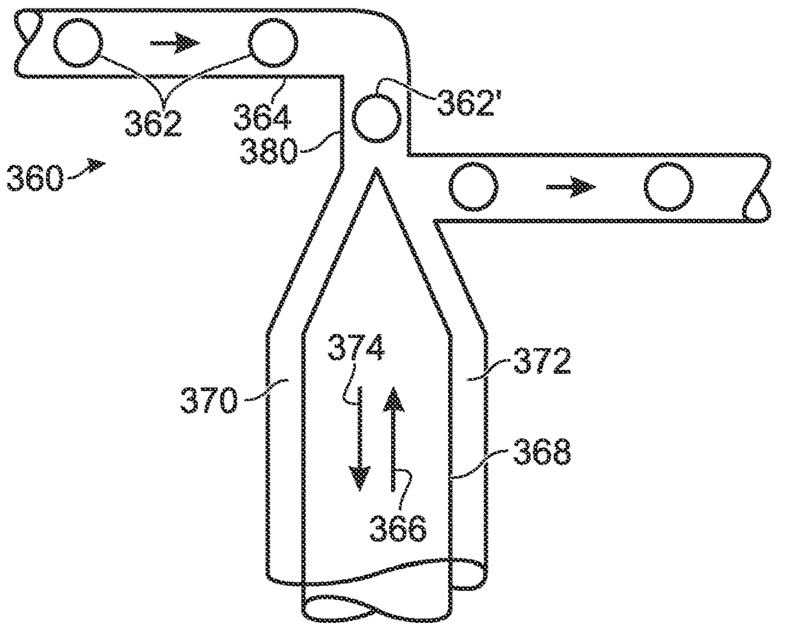
FIG. 9 depicts another intersection region configured to transmit both incident radiation and stimulated fluorescence through a single optical fiber, and also configured to transfer radiation to and from substantially one droplet at a time.

FIG. 9 depicts another intersection region, generally indicated at 360, which is similar in some respects to intersection region 340 of FIG. 8. Specifically, an optical fiber 368 in FIG. 9 is configured to transmit excitation radiation 366 from a radiation source (not shown) toward sample containing droplets 362 traveling in a fluid channel 364, and fluorescence radiation 374 from an excited droplet 362' back through the optical fiber and toward a fluorescence detector (not shown). Unlike intersection region 340, however, fluid channel 364 of intersection region 360 is oriented mostly perpendicular to the long axis of optical fiber 368, except for a "dog leg" or side-facing region 380 in the central portion of intersection region 360.

Side-facing region 380 of intersection region 360, which is configured to transport the droplets to intersection region 360 where the droplets encounter stimulating radiation transmitted by optical fiber 368, is configured to allow only a small number of droplets, such as one droplet at a time, to travel parallel to the long axis of optical fiber 368. This configuration may result in relatively more accurate detection of fluorescence radiation, because only one droplet (or a small number of droplets) is stimulated with incident radiation at a time, and only the stimulated droplet(s) emits substantial fluorescence radiation back into optical fiber 368 for detection.

Optical fiber 368 of FIG. 9 may be partially or completely surrounded by fluid, and this surrounding fluid may be in fluid communication with fluid channel 364. However, unlike fluid channels 350 and 352 of FIG. 8, fluid regions 370 and 372 surrounding optical fiber 368, which may in some cases constitute a single continuous fluid region, are too small to allow passage of any sample-containing droplets. Rather, these surrounding fluid region(s) are configured primarily to remove unnecessary interfaces between the optical fiber and the droplets, increasing the intensity of the incident radiation as described previously.

Example 3

Detection Systems with Plural Radiation Channels

In some cases, a detection system according to the present disclosure may include multiple separate incident radiation channels to illuminate sample-containing droplets that have undergone PCR thermocycling. This example describes two such systems and some of their potential uses; see FIGS. 10 and 11.

Figure 10:
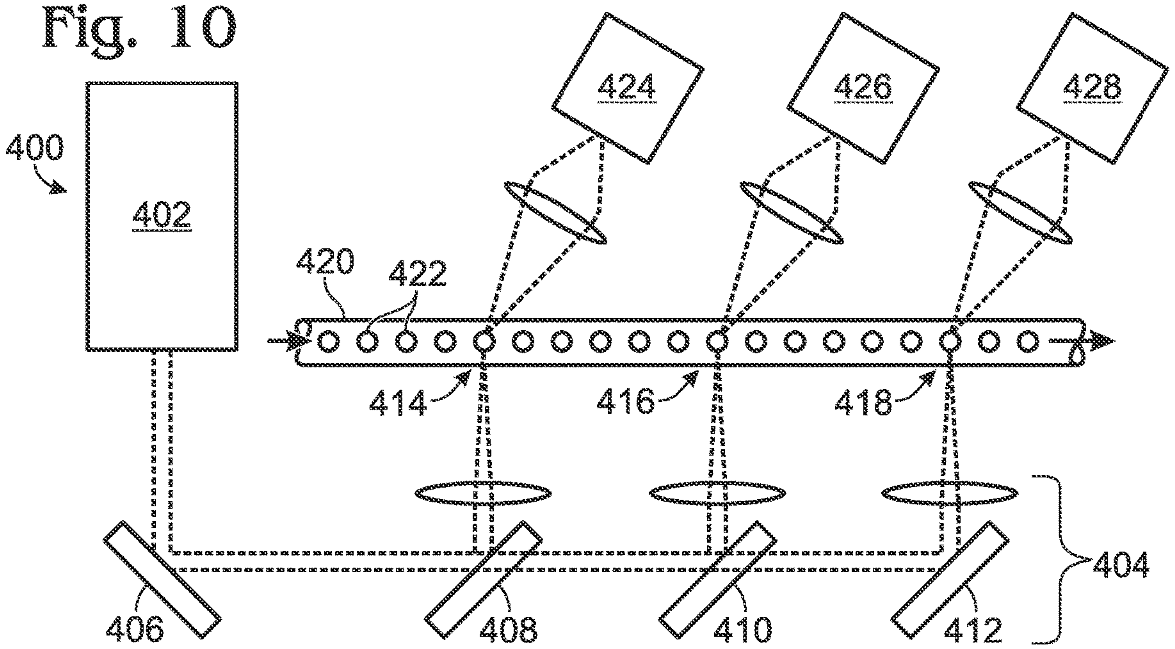
FIG. 10 is a schematic depiction of an optical detection system in which the incident radiation is split into a plurality of separate beams, in accordance with aspects of the present disclosure.

FIG. 10 depicts a multi-channel cytometry-type optical detection system, generally indicated at 400. Detection system 400 includes a radiation source 402, configured to emit radiation at one or more desired wavelengths. As described previously, a radiation source according to the present disclosure may be of various types, such as an LED source or a laser source, and may emit radiation substantially at a single wavelength, at a plurality of substantially discrete wavelengths, or within one or more ranges of wavelengths.

Radiation from source 402 passes from the source toward transmission optics, as generally indicated at 404. Transmission optics 404 may include one or more optical elements, such as a mirror 406, configured primarily to redirect radiation emitted by source 402 in a desired direction. Transmission optics 404 also may include one or more optical elements, such as reflective elements 408, 410, 412, configured to split the radiation emitted by source 402 into several different portions, each of which may be redirected in a particular manner, such as the manner shown in FIG. 10. Alternatively, radiation source 402 may be omitted, and reflective elements 408, 410, 412 each may be replaced by a separate radiation source. In some cases, providing plural radiation sources in this manner may be simpler than splitting the radiation from a single source.

In some instances, reflective elements 408, 410, 412 may be configured to transmit and reflect incident radiation in different ways. For example, reflective element 408 may be configured to reflect approximately one-third of the radiation incident upon it and to transmit approximately two-thirds of the radiation incident upon it, reflective element 410 may be configured to reflect approximately one-half of the radiation incident upon it and to transmit approximately one-half of the radiation incident upon it, and reflective element 412 may be configured to reflect substantially all of the radiation incident upon it. In this manner, radiation emitted by radiation source 402 may be split into three portions of approximately equal intensity.

In cases where it is desirable to split the radiation emitted by source 402 into a number of channels other than three, a plurality of reflective surfaces may be configured appropriately. Specifically, when n channels are desired, n reflective elements may be used, with the first reflective element configured to reflect fraction 1/n and to transmit fraction (n−1)/n of the radiation incident upon it, the second reflective element configured to reflect fraction 1/(n−1) and to transmit fraction (n−2)/(n−1) of the radiation incident upon it, the third reflective element configured to reflect fraction 1/(n−2) and to transmit fraction (n−3)/(n−2) of the radiation incident upon it, and so forth, until the last reflective element in the sequence is a pure mirror that reflects all of the radiation incident upon it and transmits none. This results in each of the n reflective elements reflecting an equal fraction 1/n of the radiation emitted by the radiation source.

An arrangement configured to split radiation from a source into several portions of either approximately equal intensity or differing intensities may be useful, for example, when it is desirable to search for various targets, each of which is bound to a fluorescent probe configured to be excited by the same wavelength of incident radiation but to fluoresce at a different wavelength. For instance, reflective surfaces 408, 410 and 412 may be configured to reflect radiation toward intersection regions 414, 416 and 418, respectively, which may be viewed as different adjacent portions of a single, larger intersection region. Similarly, when a plurality of radiation sources are used instead of reflective surfaces, each radiation source may be configured to transmit fluorescence stimulating radiation to a different adjacent portion of the intersection region.

In the intersection region(s), the arriving radiation will intersect a fluid channel 420 (such as a capillary tube) through which sample-containing droplets 422 are moving. Each droplet thus may be irradiated a plurality of times, and accordingly may be stimulated to emit fluorescence radiation a plurality of times if the irradiated droplet contains any of several desired target nucleic acid sequences. However, the droplet may emit a different wavelength of stimulated radiation depending upon which target it contains (and thus which fluorescent probe has been cleaved from its associated quenching molecule by replication of the target).

To detect stimulated fluorescence radiation corresponding to the various targets, a plurality of fluorescence detectors 424, 426, 428 may be used, with each detector positioned and oriented to receive fluorescence radiation produced at a different one of intersection regions 414, 416, 418 (or at a different portion of the larger intersection region encompassing regions 414, 416, 418). Furthermore, each fluorescence detector may be configured to detect fluorescence at a different wavelength, corresponding to one or more (but not all) of the varieties of target molecules or target nucleic acid sequences. Thus, a given irradiated droplet may emit stimulated fluorescence that is detected by just one of detectors 424, 426, 428, resulting in a "positive" detection of just one (or a subset) of the target sequences. In this manner, system 400 may be used to search for multiple targets simultaneously.

Splitting incident radiation in the manner of system 400 also may be useful when it is desirable to illuminate sample-containing droplets for more time than it takes the droplet to pass through the unsplit beam of the source. For instance, as described above, system 400 may be configured so that droplets 422 passing through a fluid channel 420 intersect radiation from source 402 at several intersection regions 414, 416, 418 corresponding to the various split beams. If these intersection regions are disposed relatively near each other, then each droplet may essentially be continuously illuminated in an area spanning all of the intersection regions 414, 416, 418. The resulting relatively long integration time (i.e., the time of exposure of a droplet to illuminating radiation) may result in greater fluorescence from each target-containing droplet, and thus in greater accuracy of the detection system. Another way to obtain a similar result is illustrated in FIG. 11 and will be described in detail below.

Still considering FIG. 10, detection system 400 also may be used to search for multiple different nucleic acid targets in cases where various probes that respond to different incident wavelengths of excitation radiation have been combined with a sample. For example, radiation source 402 may be configured to emit radiation at a plurality of discrete wavelengths or wavelength ranges, by using a plurality of radiation emitters or a single emitter configured to produce radiation at all of the desired wavelengths. In this case, each of reflective surfaces 408 and 410 (and possibly 412) may be dichroic and configured to reflect substantially all of the radiation at a particular wavelength (or within a particular wavelength range) and to transmit the remaining incident radiation. Alternatively, as described above, a plurality of radiation sources may be provided and configured to transmit fluorescence stimulating radiation at a different wavelength.

When dichroic reflective surfaces are provided, reflective surface 408 may be configured to reflect a particular wavelength or wavelength range toward intersection region 414, reflective surface 410 may be configured to reflect another particular wavelength or wavelength range toward intersection region 416, and reflective surface 412 may be configured to reflect yet another particular wavelength or wavelength range toward intersection region 418. Alternatively, reflective surface 412 may be configured to reflect all radiation toward region 418, since this will include any desired radiation that was not already reflected by surfaces 408 and 410. Accordingly, different wavelengths of incident radiation will arrive at each intersection region 414, 416, 418, and stimulated fluorescence emission will occur only if a probe sensitive to a particular arriving wavelength has been activated due to polymerase cleaving of its associated quenching molecule, i.e., only if a particular target is present. Detectors 424, 426, 428 may be used to monitor the activation of droplets within the various intersection regions, as described previously.

Figure 11:
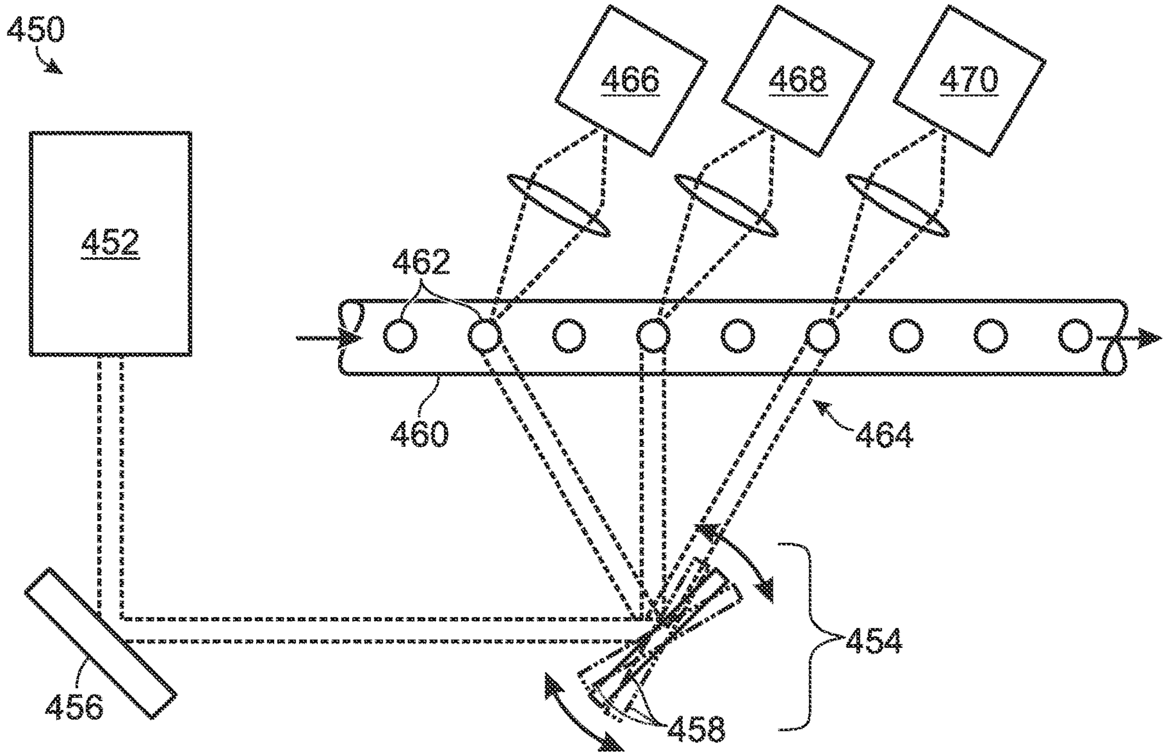
FIG. 11 is a schematic depiction of an optical detection system in which the incident radiation is spread by an adjustable mirror into a relatively wide intersection region, in accordance with aspects of the present disclosure.

FIG. 11 depicts another multi-channel cytometry-type optical detection system, generally indicated at 450. System 450 is generally similar to system 400, including a radiation source 452 and transmission optics generally indicated at 454. In the case of system 450, the transmission optics may include first and second mirrors 456, 458 configured to redirect radiation emitted by source 452 in a desired manner. Transmission optics 454 also may include one or more other optical elements (not shown) for focusing radiation from source 452, as described previously.

As indicated in FIG. 11, mirror 458 may be adjustable so that it is configured to reflect radiation at a range of different angles, to direct it toward a range of different positions along a fluid channel 460 through which sample-containing droplets 462 are being transferred. Thus, the reflected radiation defines an intersection region, generally indicated at 464, which is substantially wider than it would be if mirror 458 was fixed in a single orientation. If mirror 458 is adjusted relatively rapidly, this configuration may allow radiation from source 452 to illuminate more than one droplet at a time, or may cause a single droplet to fluoresce at various positions within fluid channel 460. In this case, a plurality of detectors 466, 468, 470 may be oriented to look for radiation at particular wavelengths corresponding to various target probes.

Alternatively, if the adjustment speed of mirror 458 is chosen to correspond to the known approximate speed of sample-containing droplets traveling within fluid channel 460, then the mirror may effectively increase the illumination time of each droplet by "tracking" the droplet through the channel. In this case, it may be appropriate to use only a single fluorescence detector, with a field of view that spans the entire path traveled by a droplet during its illumination.

Example 4

Separation of Droplets

Figure 12:
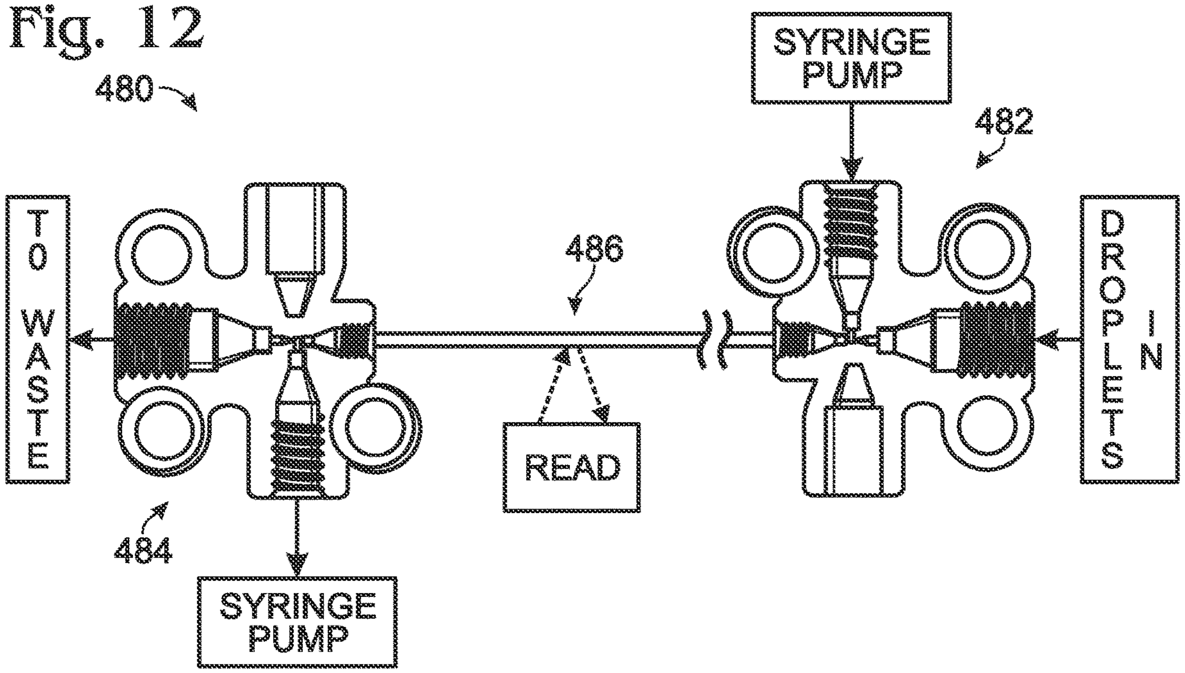
FIG. 12 depicts a detection system for droplet-based assays, including a droplet singulator, in accordance with aspects of the present disclosure.
Figure 13:
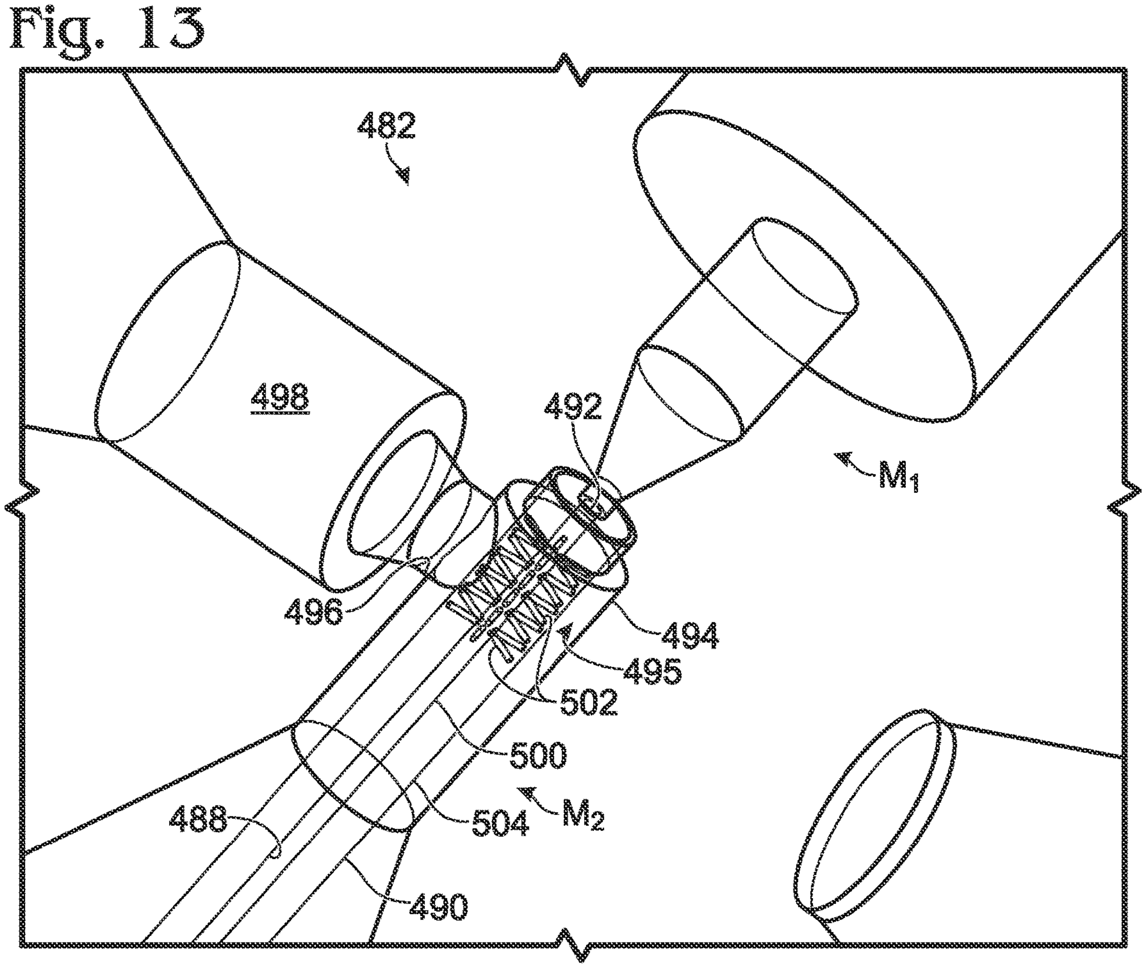
FIG. 13 is a magnified view of a central portion of the droplet singulator of FIG. 12.

This example describes mechanisms for achieving a desired separation between particles, for example sample-containing droplets as they pass through a fluorescence detection system; see FIGS. 12-14. As the discussion above indicates, it may be desirable for droplets within a detection region to be separated by some known average distance, or at least by some approximate minimum distance. For example, adequate spacing may permit split beams of radiation and/or detectors to be disposed most appropriately, and may allow a suitable choice of adjustment range for an adjustable mirror, when one is used.

In addition, proper spacing can help to avoid unintentionally detecting radiation from two or more droplets simultaneously, which can result in false positives and other errors in the detection system. For instance, as described previously, an uncleaved probe within a droplet still emits some amount of fluorescence even though the nucleic acid target is not present in the droplet. Thus, the intensity of fluorescence emitted from two or more droplets, neither of which contains a target, may be sufficient to trigger a positive detection result if the fluorescence from those multiple droplets is mistakenly thought to come from a single droplet. Other errors, such as errors in determining droplet volume and target concentration, also may result when droplets are spaced too closely together.

FIG. 12 schematically depicts a detection system for droplet-based assays, generally indicated at 480. Detection system 480 includes both a droplet separator, spacer, or singulator, generally indicated at 482, and a carrier fluid extractor, generally indicated at 484. A detection region, generally indicated at 486, is disposed between the droplet singulator and the carrier fluid extractor.

The droplet singulator is configured to separate sample-containing droplets from each other by some desired amount of distance. This mechanism may be used, for example, to separate droplets prior to transferring them toward a detector intersection region such as detection region 486, intersection region 214 of FIG. 2, intersection region 264 of FIG. 4, or any of the other detection regions described above. Exemplary droplet singulator structures are described below in more detail.

Carrier fluid extractor 484, as FIG. 12 suggests, may have a structure similar to the structure of droplet singulator 482. However, the carrier fluid extractor is configured to reduce the volume of fluid in the system, rather than to increase the volume of fluid. In other words, the carrier fluid extractor can be thought of as a droplet singulator operated in reverse. Reducing the volume of fluid may have various purposes. For example, carrier fluid volume reduction will generally increase the concentration of droplets and/or other sample particles flowing through the system. In addition, the carrier fluid extractor may be used to remove oil droplets from the system or to recover excess oil, which then may be filtered or otherwise decontaminated, recycled, and/or reused.

Detection region 486 is generally disposed downstream from the droplet singulator, and may include any suitable detector configured to detect droplets or other particles of interest. For example, detection region 486 may include a detector configured to detect radiation, such as fluorescence radiation, emitted by droplets passing through the detection region. For example, detection region 486 may include any of the radiation sources, optical elements (e.g., lenses and mirrors), and/or detectors described above and depicted in FIGS. 2-11.

FIG. 13 shows a magnified view of a central portion of droplet singulator 482, and a similar description may be made of the central portion of. The droplet singulator includes a droplet channel 488 formed in and/or passing through an inner cylinder 490, such as an amorphous silica capillary, and having a droplet inlet 492 configured to receive droplets of sample fluid suspended in a carrier fluid. An outer shell 494 surrounds a portion of droplet channel 488 and inner cylinder 490, and is configured to receive dilution fluid that may be transported into droplet channel 488. In the exemplary structure of FIG. 13, shell 494 is cylindrical, and inner cylinder 492 is disposed coaxially within the shell, leaving a hollow region or void 495 between the inner cylinder and the outer shell. In some examples, shell 494 and inner cylinder 492 may be shaped or configured differently than depicted. For example, shell 494 and/or inner cylinder 492 may be tapered, irregular, oblique, cuboidal, pyramidal, spherical, or the like, or any combination thereof. A dilution fluid channel 496 is formed in outer shell 494 and configured to receive dilution fluid from a dilution fluid source 498 disposed outside the shell.

In this example, inner cylinder 490 has a central bore 500 running along a central longitudinal axis of the inner cylinder and defining the portion of droplet channel 488 surrounded by the shell, and a plurality of radial bores 502 extending between central bore 500 and an outer surface 504 of inner cylinder 490. Radial bores 502 form a plurality of dilution channels configured to transport dilution fluid from the region between the outer shell and the inner cylinder to the droplet channel at a controlled rate. In this context, the inclusion of radial bores in the inner cylinder may be described as porous walls surrounding the central axial bore or droplet/particle channel, and the inner cylinder may be described as a filter. The controlled infusion of dilution fluid into the droplet channel allows droplets to be spaced apart by any desired distance, depending on the flow of dilution fluid through the dilution channels.

Radial bores 502 may be formed, for example, by laser drilling and/or any other suitable method. Furthermore, bores 502 may be provided with uniform diameter and separation distance from each other, or the bores may be spaced nonuniformly and/or provided with differing diameters and/or following pathways of different lengths, directions, linearities, tortuosities, and/or angles, resulting in various dilution characteristics such as gradual, aggressive, multistage, or nonuniform infusion rates of dilution fluid. This allows the singulator to control the acceleration and/or spacing of the droplets passing through the dilution region in a variety of predictable and/or desired ways.

FIG. 14 is a magnified sectional view depicting another droplet singulator 510 suitable for use with a detection system such as system 480, in place of, or in addition to, the radial bore configuration of droplet singulator 482. Singulator 510 is similar in many ways to singulator 482, including a droplet channel 512 having a droplet inlet 514 configured to receive droplets of sample fluid suspended in a carrier fluid, a shell 516 surrounding at least a portion of the droplet channel, and a plurality of dilution channels 518 formed within the shell and configured to transport dilution fluid to the droplet channel at a controlled rate, to separate droplets traversing the droplet channel by a desired distance.

Singulator 510 includes a porous filter 520 having dilution channels 518 that allow dilution fluid to pass between shell 516 and droplet channel 512 passing through the porous filter. This arrangement may be described as an infusion singulator having a porous media generally surrounding a capillary. Porous filter 520 may take the form of a cylindrical or tubular frit disposed within shell 516, the frit having porous walls and a central bore 522 defining a portion of the droplet channel surrounded by the shell. In this example, dilution channels 518 are formed by the pores of the frit, and the frit may be described as having porous walls. A frit or other porous device such as filter 520 may include any suitable structure having a substantially uniform porosity and/or pore distribution, irregular and/or tortuous pore pathways, and configured to facilitate passing a dilution fluid therethrough without passing droplets or other particles of interest. In some examples, porous filter 520 may include a glass, ceramic, metallic (e.g. stainless steel), and/or plastic (e.g. polyethylene) frit. In some examples, porous filter 520 may take the form of a capillary or filter having porous walls and a central bore defining the portion of the droplet channel surrounded by the shell, in which case the dilution channels are formed by the porous walls of the capillary or filter. Accordingly, addition of carrier fluid may be radially symmetrical and may be distributed, either uniformly or predictably, along a length of the droplet channel, thereby reducing stress caused by the infusion on the droplets or other particles of interest.

The porous filter and outer shell of singulator 510 may take any suitable form or shape, as described above regarding outer shell 494 and inner cylinder 490. For example, porous filter 520 may be tapered, irregular, oblique, cylindrical, cuboidal, conical, spherical, and/or pyramidal, or the like, or any combination thereof. In other words, in some examples, filter 520 may be a porous cylinder, porous sphere or porous cuboid having a central bore. The shape or form of porous filter 520 may be selected to achieve different droplet-spacing results. For example, a tapered structure such as a truncated cone may result in shorter dilution fluid pathways at the smaller end of the cone than at the larger end, with corresponding effects on droplets passing through a central bore. Similarly, shell 516 may include any suitable shape either corresponding to the shape of porous filter 520, or not.

The above examples are described in terms of their use in spacing droplets by adding carrier fluid to the droplet channel. It is again noted that these devices may also or instead be used in the opposite manner to reduce the volume of carrier fluid, which may include water, oil, air, or the like, from a droplet sample. This may, for example, be done to increase a concentration of droplets, cells, particles, or the like.

In examples described above and depicted in FIGS. 12-14, the droplet singulator may be modular. For example, in FIG. 13, a first module M1 may include outer shell 492 and inner cylinder 494, and a second module M2 may include a microfluidic "T" fitting into which these concentric elements are installed. Similarly, in FIG. 14, a first module M1' may include outer shell 516 and inner porous filter 520 (i.e., the frit, capillary, or filter), and a second module M2' may include a microfluidic "T" fitting into which these concentric elements are installed.

Example 5

Batch Fluorescence Detection

In some cases, it may be desirable to irradiate and/or detect fluorescence from sample-containing droplets in relatively large batches rather than one droplet at a time. This example describes a system for detecting fluorescence emitted from a plurality of droplets that have been transferred to a chamber for batch detection; see FIG. 15.

Figure 15:
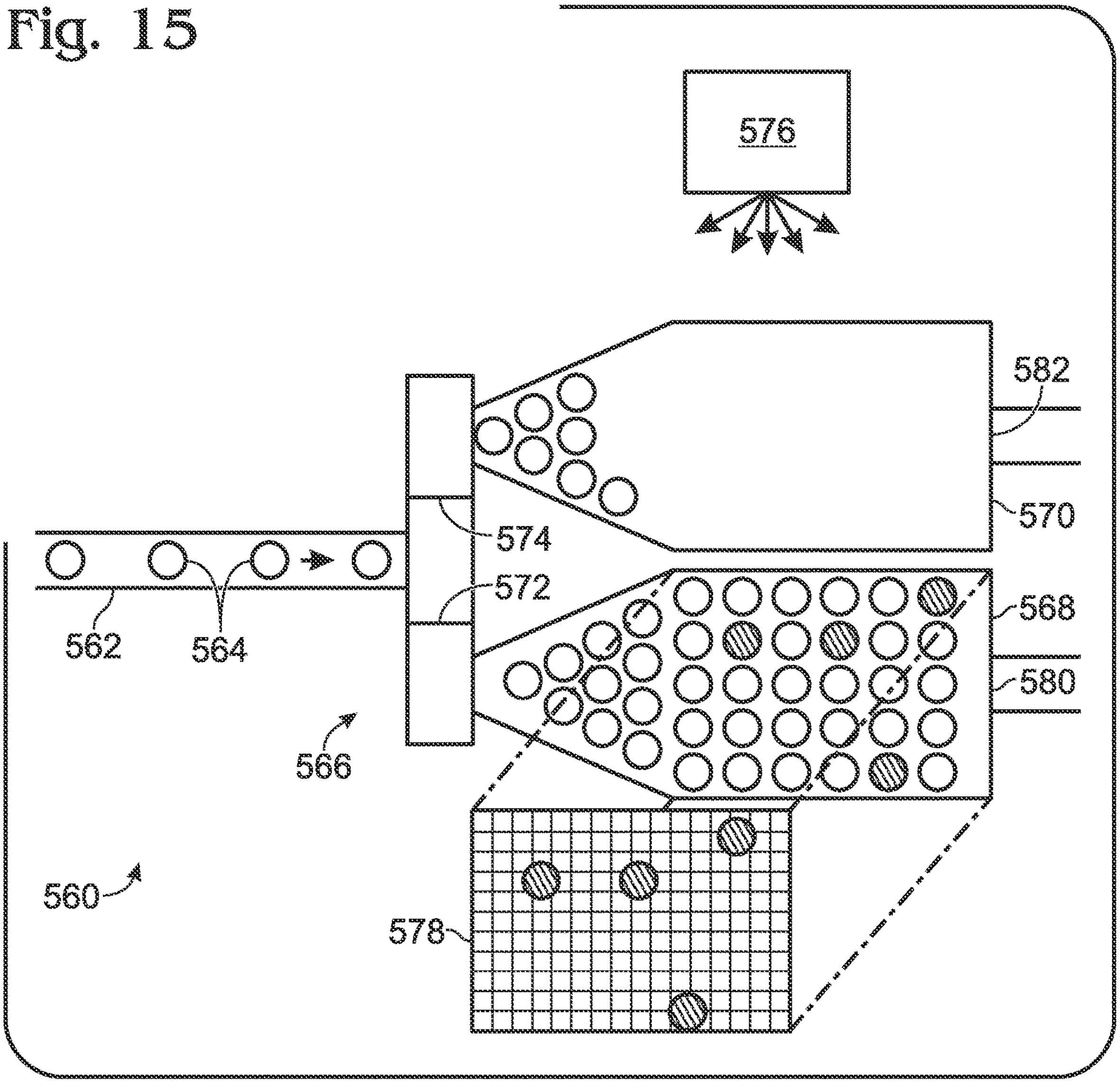
FIG. 15 depicts a batch fluorescence detection system, in accordance with aspects of the present disclosure.

FIG. 15 schematically depicts a batch optical detection system, generally indicated at 560. In contrast to the previously described continuous flow detection systems, in which sample-containing droplets flow continuously through an intersection region where excitation radiation intersects the path of the moving droplets, system 560 is configured to detect radiation from a plurality of droplets that have been collected in a detection region, and in some cases temporarily stopped from flowing through the system. This allows the fluorescence level of many droplets to be detected in a single detection operation, which may be advantageous in some applications.

Batch detection system 560 includes a droplet input channel 562, within which sample-containing droplets 564 may be caused to flow in an emulsion (such as a water-in-oil emulsion), just as in the previously described detection systems. System 560 also includes a valve mechanism, generally indicated at 566, which is configured to selectively direct droplets toward either of two fluorescence detection chambers 568, 570. For example, valve mechanism 566 may include a first valve 572 disposed between droplet input channel 562 and detection chamber 568, and a second valve 574 disposed between droplet input channel 562 and detection chamber 570. Thus, by opening and closing valves 572 and 574 appropriately, droplets may be transferred selectively into chambers 568, 570. This may allow a substantially continuous flow of emulsion to be transferred from the droplet input fluid channel to the fluorescence detection chambers.

Chambers 568, 570 may be configured to have a relatively shallow depth, to allow substantially only a monolayer of droplets within each chamber, so that only one droplet is disposed within each portion of the line of sight of a detector and is confined to the focal plane of the detector. Alternatively, various three-dimensional detection configurations, such as confocal imaging or wide-field imaging with deconvolution, may be used with non-monolayer samples.

A radiation source 576 is configured to illuminate droplets within chambers 568, 570, and after a desired number of droplets are transferred into one of the detection chambers, the chamber may be illuminated with radiation from source 576. Source 576 may be configured in various ways to illuminate substantially all of the droplets within a chamber. For example, radiation source 576 may include a single radiation emitting element, configured to illuminate substantially the entire chamber either by emitting a broad beam of radiation or by emitting radiation toward intermediate optics (not shown) that spread the emitted beam to cover the entire chamber. The radiation source also may include a plurality of radiation emitting elements, such as lasers, LEDs, and/or lamps, among others, each configured to illuminate a portion of the appropriate detection chamber. Alternatively or in addition, one or more radiation emitting elements of radiation source 576 may be configured to scan the chamber, to sequentially illuminate droplets within the chamber, or the chamber itself may be configured to move so that all portions of the chamber intersect a substantially stationary beam of radiation. In some cases, a combination of two or more of the above techniques may be effective.

A fluorescence detector 578 is provided and configured to detect fluorescence emitted from droplets 564. As has been described previously, the amount of fluorescence emitted by a particular droplet is expected to be significantly higher if the droplet contains a target nucleotide sequence, because in that case the corresponding fluorescent probe will typically have been cleaved from its associated quenching molecule. Thus, after the droplets within a detection chamber have been illuminated with stimulating radiation or in some cases while illumination is occurring, detector 578 may be configured to receive fluorescence from the detection chamber. As in the case of illumination, detection may proceed in various ways. For example, a large format detector such as a CCD focal plane array may be used to detect radiation emitted from an entire detection chamber simultaneously. Alternatively, a smaller detector such as a photodiode or a photomultiplier may be scanned across the chamber, or the chamber may be repositioned with respect to the detector, to detect fluorescence radiation from various portions of the detection chamber sequentially.

System 560 may be configured to allow substantially continuous flow through droplet input channel 562, by transferring droplets into two or more detection chambers, such as chambers 568, 570, sequentially. For example, FIG. 15 depicts the system at a time when chamber 568 has already been filled with droplets and is being illuminated and/or imaged, whereas chamber 570 is in the process of being filled. Accordingly, valve 572 will be in its closed position, and valve 574 will be in its open position, to allow droplets to flow into chamber 570.

Upon completion of the detection process on the droplets within chamber 568, valve 574 may be closed, valve 572 may be opened, and another valve 580 at the distal end of chamber 568 also may be opened. This stops the flow of droplets into chamber 570 and restarts the flow of droplets into chamber 568, while allowing the droplets already in chamber 568 to escape through distal valve 580. Another distal valve 582 may be disposed at the end of chamber 570 for a similar purpose. Alternatively, before the flow of droplets into a given chamber is resumed, and while droplets are still flowing into the other chamber, the chamber not receiving droplets may be washed with a fluid that enters through another fluid channel (not shown). This may help to avoid the possibility of mistakenly illuminating and detecting the same droplet twice. With or without a wash step, coordinated motions of valves as described above may allow an emulsion of sample-containing droplets to be continuously transferred in and out of any desired number of detection chambers.

Batch fluorescence detection may be performed without actually stopping droplets within the detection chambers of the system. For example, even if valves 580, 582 are not provided or are left open, droplets entering one of chambers 568, 570 may slow sufficiently to allow batch detection, and the lateral width of the detection chambers may be chosen to facilitate this. Alternatively or in addition, various particle tracking algorithms may be used to track droplets as they move within the detection chambers. Furthermore, a batch detection system may be partially or completely fluidically decoupled from other portions of a molecular amplification system. For example, a simple array of droplet-containing wells or reservoirs (such as a plate array) may be placed in a fluorescence detection region and imaged as described above.

Example 6

Detection Methods

This example describes a method of detecting fluorescence from sample-containing droplets that have undergone PCR thermocycling; see FIG. 16.

FIG. 16 is a flowchart depicting the steps of a fluorescence detection method, generally indicated at 600, which may be performed in conjunction with a PCR system of DNA amplification according to the present disclosure. Although various steps of method 600 are described below and depicted in FIG. 16, the steps need not necessarily all be performed, and in some cases may be performed in a different order than the order shown in FIG. 16.

At step 602, sample-containing droplets suspended in a carrier fluid are transported into a droplet channel. This may be accomplished manually, for instance using a syringe, or automatically (or semi-automatically) within an apparatus that also performs other functions such as sample preparation and/or thermocycling, among others. At step 604, the sample-containing droplets are transported downstream through the droplet channel to a dilution region. This will generally be accomplished through the application of pressure (positive and/or negative) at one or more suitable points which are fluidically connected to the droplet channel.

At step 606, dilution fluid is transported into a shell surrounding at least a portion of the droplet channel. For example, dilution fluid may be transported into the shell from a dilution fluid source through a dilution fluid input channel, as depicted in FIGS. 13 and 14 and described above. At step 608, dilution fluid is transported from the shell into the droplet channel at a controlled rate through a plurality of dilution channels formed inside the shell, increasing the average distance between droplets disposed within the droplet channel to a desired degree. The dilution channels may be formed, for example, as a plurality of radial bores in an inner cylinder (see FIG. 13), or as a plurality of channels in the walls of a suitable porous cylinder such as a frit, capillary, or filter (see FIG. 14). In some cases, the shell and inner cylinder may form a module configured to interface with a standard microfluidic "T" connector. In other cases, all of these elements may be specially manufactured.

At step 610, the spaced-apart droplets are transported from the dilution region to a detection region, and at step 612, fluorescence radiation emitted by droplets passing through the detection region is detected. Transporting the droplets to the detection region may be performed as part of a continuous flow, in which the droplets simply continue their downstream motion from the dilution region until they arrive at the detection region. Alternatively, the droplets may be transported to the detection region in a discontinuous flow process by a dedicated transport system, such as the transport system described below in Example 7 and as depicted, for example, in FIG. 17. The detection region and the detection of emitted radiation may be as described above in Examples 1-3 and as depicted, for example, in FIGS. 2-11.

Example 7

Exemplary Transport System for Detection

Figure 17:
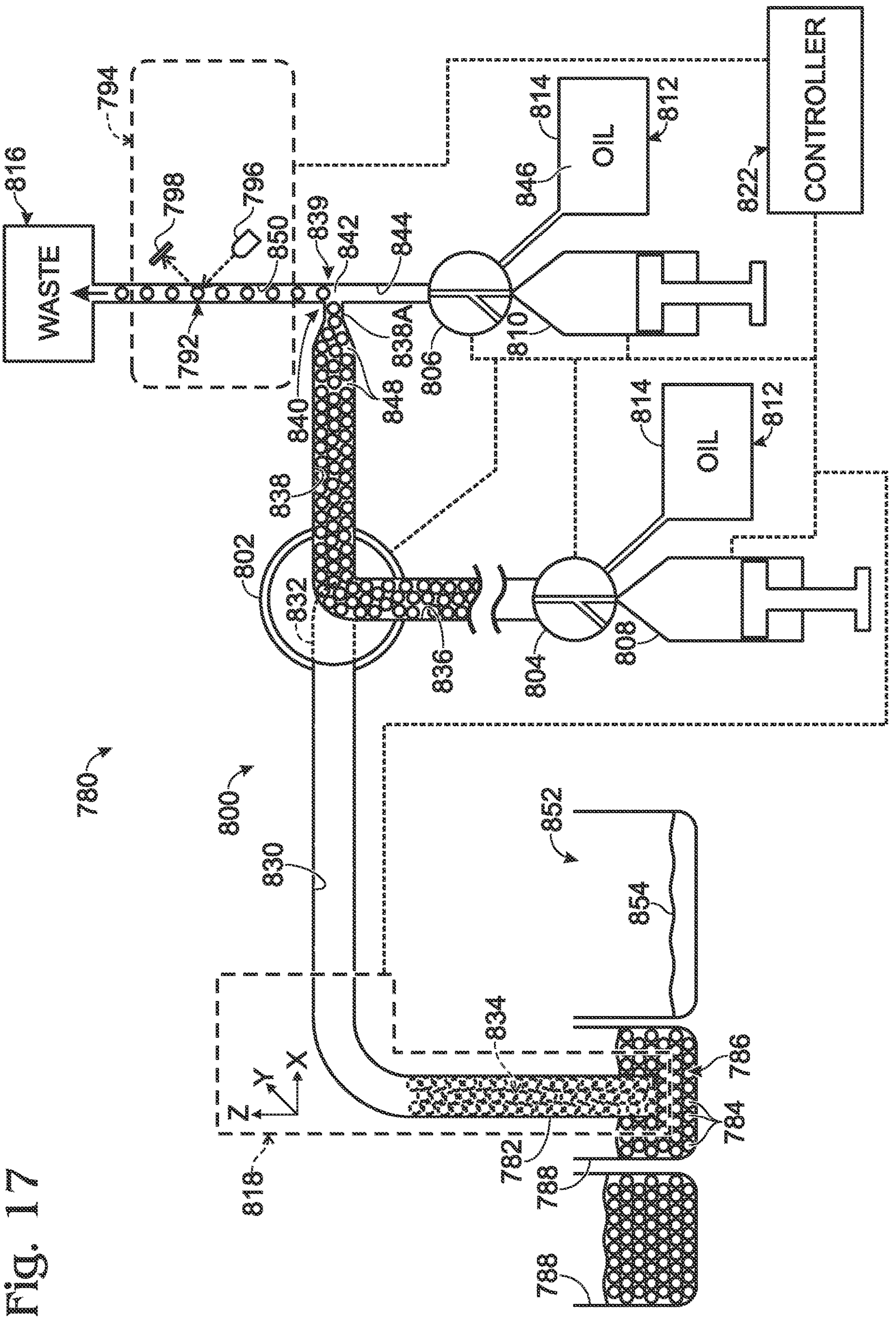
FIG. 17 is a schematic view of selected aspects of an exemplary droplet transport system for picking up droplets from a container, increasing the distance between droplets, and driving the droplets serially through an examination region for detection, in accordance with aspects the present disclosure.

This example describes an exemplary transport system 80 for loading droplets, spacing droplets, and driving the spaced droplets to an examination region for detection; see FIG. 17.

Transport system 780 is configured to utilize a tip 782 to pick up droplets 784 in an emulsion 786 held by at least one container 788. The droplets may be queued and separated in a droplet arrangement region 790, and then conveyed serially through an examination region 792 for detection of at least one aspect of the droplets with at least one detection unit 794. The detection unit may include at least one light source 796 to illuminate examination region 792 and/or fluid/droplets therein, and at least one detector 798 to detect light received from the illuminated examination region (and/or fluid/droplets therein).

The transport system may include a channel network 800 connected to tip 782. The channel network may include channel-forming members (e.g., tubing and/or one or more chips) and at least one valve (e.g., valves 802-806, which may include valve actuators) to regulate and direct fluid flow into, through, and out of the channel network. Fluid flow into, through, and out of channel network 800 may be driven by at least one pressure source (to apply negative pressure and/or positive pressure), generally, a pump, such as a sample pump 808 and a dilution pump 810. The fluid introduced into channel network 800 may be supplied by emulsion 786 and one or more fluid sources 812 formed by reservoirs 814 and operatively connected to one or more of the pumps. (A cleaning fluid also may be introduced via the tip.) Each fluid source may provide any suitable fluid, such as a hydrophobic fluid (e.g., oil), which may be miscible with the continuous phase of the emulsion and/or a carrier phase in the system, but not the dispersed phase of the droplets, or may provide a relatively more hydrophilic fluid for cleaning portions of the channel network and/or tip. Fluid that travels through examination region 792 may be collected in one or more waste receptacles 816.

The continuous phase, carrier fluid, and/or dilution fluid may be referred to as oil or an oil phase, which may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others. In exemplary embodiments, the oil is a fluorinated oil, such as a fluorocarbon oil, which may be a perfluorinated organic solvent. A fluorinated oil includes fluorine, typically substituted for hydrogen. A fluorinated oil may be polyfluorinated, meaning that the oil includes many fluorines, such as more than five or ten fluorines, among others. A fluorinated oil also or alternatively may be perfluorinated, meaning that most or all hydrogens have been replaced with fluorine. An oil phase may include one or more surfactants.

Each pressure source or pump may have any suitable structure capable of driving fluid flow. The pump may, for example, be a positive-displacement pump, such as a syringe pump, among others. Other exemplary pumps include peristaltic pumps, rotary pumps, or the like.

The position of tip 782 may be determined by a drive assembly 818 capable of providing relative movement of the tip and container(s) 788 along one or more axes, such as three orthogonal axes 820 in the present illustration. In other words, the drive assembly may move the tip while the container remains stationary, move the container while the tip remains stationary, or move both the tip and the container at the same or different times, among others. In some embodiments, the drive assembly may be capable of moving the tip into alignment with each container (e.g., each well of a multi-well plate), lowering the tip into contact with fluid in the container, and raising the tip above the container to permit movement of the tip to another container. The drive assembly may include one or more motors to drive tip/container movement, and one or more position sensors to determine the current position of the tip and/or container and/or changes in tip/container position. Accordingly, the drive assembly may offer control of tip position in a feedback loop.

Transport system 780 further may include a controller 822. The controller may control operation of, receive inputs from, and/or otherwise communicate with any other components of the transport system, such as detection unit 794, valves 802-806 (e.g., via actuators thereof), pumps 808 and 810, and drive assembly 818, among others. For example, the controller may control light source operation and monitor the intensity of light generated, adjust detector sensitivity (e.g., by adjusting the gain), process signals received from the detector (e.g., to identify droplets and estimate target concentrations), and so on. The controller also or alternatively may control valve positions, tip movement (and thus tip position), pump operation (e.g., pump selection, direction of flow (i.e., generation of positive or negative pressure), rate of flow, volume dispensed, etc.), and the like. The controller may control when, where, and how fluid moves within the channel network 800. The controller may provide automation of any suitable operation or combination of operations. Accordingly, the transport system may be configured to load and examine a plurality of emulsions automatically without user assistance or intervention.

The controller may include any suitable combination of electronic components to achieve coordinated operation and control of system functions. The electronic components may be disposed in one site or may be distributed to different areas of the system. The controller may include one or more processors (e.g., digital processors, also termed central/computer processing units (CPUs)) for data processing and also may include additional electronic components to support and/or supplement the processors, such as switches, amplifiers, filters, analog to digital converters, busses, one or more data storage devices, etc. In some cases, the controller may include at least one master control unit in communication with a plurality of subordinate control units. In some cases, the controller may include a desktop or laptop computer. In some cases, the controller only may process data. The controller may be connected to any suitable user interface, such as a display, a keyboard, a touchscreen, a mouse, etc.

Channel network 800 may include a plurality of channels or regions that receive droplets as the droplets travel from tip 782 to waste receptacle 816. The term "channel" may be used interchangeably with the term "line" in the explanation and examples to follow.

Tip 782 may form part of an intake channel or loading channel 830 that extends into channel network 800 from tip 782. Droplets may enter other regions of the channel network from loading channel 830. Droplets 784 in emulsion 786 may be introduced into loading channel 830 via tip 782 (i.e., picked up by the tip) by any suitable active or passive mechanism. For example, emulsion 786 may be pulled into the loading channel by a negative pressure created by a pump, i.e., by suction (also termed aspiration), may be pushed into the loading channel by a positive pressure applied to emulsion 786 in container 788, may be drawn into the loading channel by capillary action, or any combination thereof, among others.

In exemplary embodiments, pump 808 pulls the emulsion into loading channel 830 by application of a negative pressure. To achieve loading, valve 802 may be placed in a loading position indicated in phantom at 832, to provide fluid communication between tip 782 and pump 808. The pump then may draw the emulsion, indicated by phantom droplets at 834, into loading channel 830 via tip 782, with the tip in contact with the emulsion. The pump may draw the loaded droplets through valve 802 into a holding channel 836.

The loaded droplets may be moved toward detection unit 794 by driving the droplets from holding channel 836, through valve 802, and into a queuing channel 838 that extends to an inlet channel 838A of a spacer 839, which in this case is T-shaped. Inlet channel 838A may place the droplets in single file, indicated at 840.

The droplets may enter a confluence region or separation region 842 of spacer 839, optionally in single file, as they emerge from inlet channel 838A. The confluence region may be formed at a junction of the inlet channel and at least one dilution channel 844. The dilution channel may supply a stream of dilution fluid 846 driven through confluence region 842, as droplets and carrier fluid/continuous phase 848 enter the confluence region as a stream from inlet channel 838A. The dilution fluid may be miscible with the carrier fluid and serves to locally dilute the emulsion in which the droplets are disposed, thereby increasing the average distance between droplets.

The spacer may define a minimum diameter of a flow path that droplets follow from tip 782 through examination region 792, and optionally to a waste receptacle downstream of the examination region. Further aspects of spacers are described below in Examples 8-11.

The droplets may enter an examination channel 850 after they leave spacer 839. The examination channel may include examination region 792, where the examination channel may be illuminated and light from the examination region may be detected.

Tip 782 may be utilized to load a series of emulsions from different containers. After droplets are loaded from a first container, the tip may be lifted to break contact with remaining fluid, if any, in the container. A volume of air may be drawn into the tip to serve as a barrier between sets of loaded droplets and/or to prevent straggler droplets from lagging behind as the droplets travel through the channel network. In any event, the tip next may be moved to a wash station 852, wherein tip 782 may be cleaned by flushing, rinsing, and/or immersion. More particularly, fluid may be dispensed from and/or drawn into the tip at the wash station, and the tip may or may not be placed into contact with a fluid 854 in the wash station during cleaning (e.g., decontamination). The cleaned tip then may be aligned with and lowered into another container, to enable loading of another emulsion.

A transport system may include any combination of at least one vessel (i.e., a container) to hold at least one emulsion (and/or a set of vessels to hold an array of emulsions), at least one pick-up tip to contact the emulsion(s) and receive droplets from the emulsion, one or more fluid drive mechanisms to generate positive and/or negative (i.e., one or more pumps to pull and/or push fluid into or out of the tip and/or through a detection site), a positioning mechanism for the tip and/or vessel (to move the tip with respect to the vessel or vice versa), one or more valves to select and change flow paths, at least examination region to receive droplets for detection, or any combination thereof, among others.

Example 8

Detection System with a Cross-Shaped Spacer

Figure 18:
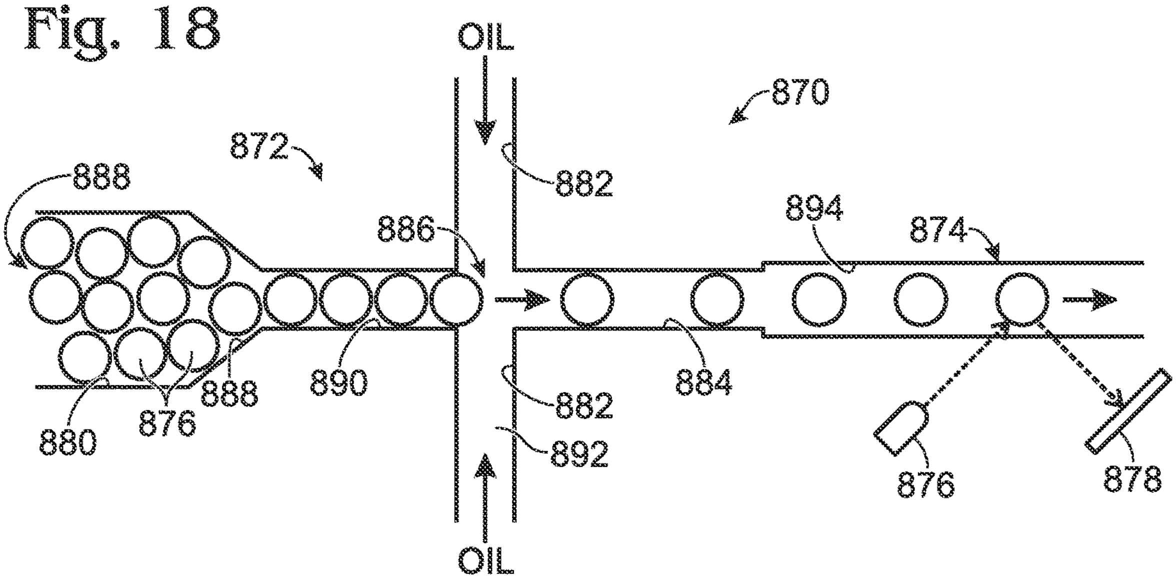
FIG. 18 is a schematic view of an exemplary detection system including a cross-shaped spacer positioned upstream of an examination region where light is detected from droplets, in accordance with aspects of the present disclosure.
Figure 19:
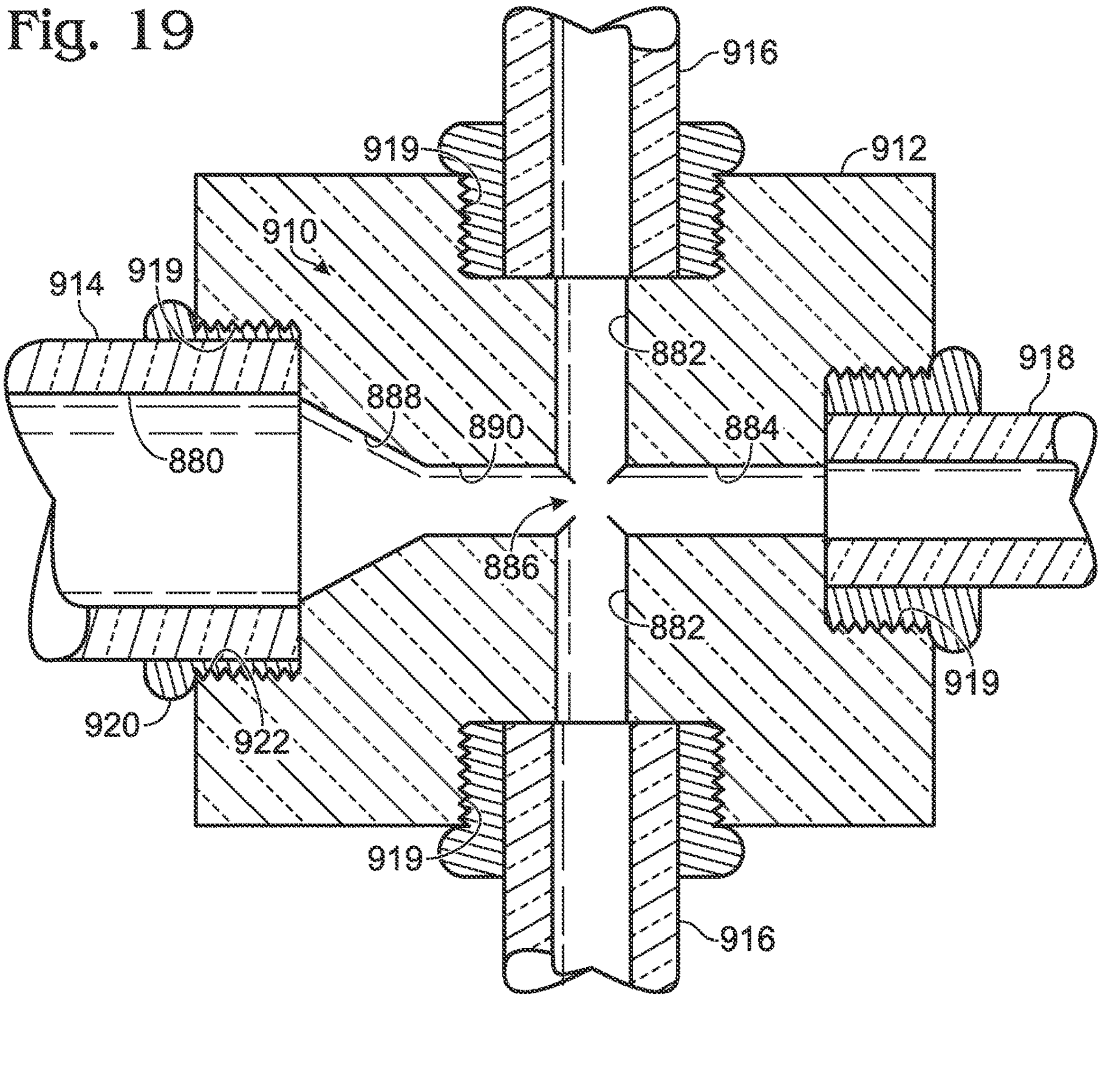
FIG. 19 is a sectional view of another exemplary cross-shaped spacer that may be included in the detection system of FIG. 18, in accordance with aspects of the present disclosure.

This example describes an exemplary detection system including a cross-shaped spacer; see FIGS. 18 and 19. The detection system in this example and in Examples 9-11 also or alternatively may be described as a transport system for detection and may include any combination of the components, features, and capabilities of the transport systems described in Example 7 and in U.S. Provisional Patent Application Ser. No. 61/467,347, filed Mar. 24, 2011, which is incorporated herein by reference.

FIG. 18 shows an exemplary detection system 870 including a cross-shaped spacer 872 positioned upstream of an examination region or irradiation zone 874. Droplets 876 may be placed in single file and separated from each other by spacer 872. The separated droplets then may travel serially through examination region 874 where they are illuminated with at least one light source 876. Light from the droplets and/or examination region may be detected by at least one detector 878.

Spacer 870 may include a droplet inlet channel 880, a pair of dilution channels 882, and a droplet outlet channel 884. A confluence region 886 may be formed where the channels meet.

In operation, an emulsion 888 containing droplets 876 flows along droplet inlet channel 880 to confluence region 886. Inlet channel 880 may include neck region, such as a tapered region 888 and a uniform region 890, in which the droplets may be disposed in single file before they enter confluence region 886. The uniform region may be of substantially uniform diameter and may define a minimum diameter of a flow path followed by droplets from a tip to an examination region of a detection system (e.g., see FIG. 17).

Dilution channels 882 supply a dilution fluid 892, such as oil, to the confluence region. The dilution fluid dilutes emulsion 888 locally, which increases the average distance between the droplets and may accelerate each droplet out of the confluence region into droplet outlet channel 884. The spacer reduces the density of the droplet emulsion (i.e., reduces the number of droplets per μL and/or per unit length of the flow path). This dilution may be advantageous when droplet detection occurs in a flow-through detector as it reduces the rate at which coincident droplets pass through the examination region.

Examination region 874 may be formed by an examination channel 894 that extends from droplet outlet channel 884. The examination channel may be discrete from the droplet outlet channel and may have the same or a different diameter, such as a larger diameter as shown here.

Droplet inlet channel 880 may have any suitable shape and size. Tapered region 888 of channel 880 may converge in a substantial cone from a diameter of two or more droplet diameters to a minimum diameter of approximately one droplet diameter or less than one droplet diameter. Uniform region 890 may define a minimum diameter of the flow path followed by droplets, and may extend for any suitable length such as at least one droplet (or channel) diameter, two or more droplet (or channel) diameters, or at least about three droplet (or channel) diameters, among others. Exemplary lengths may include between about one-half and three average droplet diameters, between about one and two droplet average diameters, and between about five-fourths and two average droplet diameters, among others. A relatively longer uniform region of the droplet inlet channel may permit greater droplet stabilization before droplets are subjected to shear force in the confluence region.

Dilution channels 882 may have any suitable diameter. Channels 882 may, for example, be about one-fifth of the droplet diameter to about two droplet diameters, among others. In some examples, the droplets may be about 125 microns in diameter and the oil channels about 25 microns to about 250 microns in diameter. Shear produced in the confluence region by inflow of dilution fluid can be reduced by increasing the diameter of the dilution channels, but if the diameter is too large, two droplets can pass through together. Generally, smaller diameter channels and/or higher flow rates can cause higher shear stresses.

Droplet outlet channel 884 may have any suitable size(s). Channel 884 may have a diameter that is about the same as or greater than the minimum diameter of droplet inlet channel 880.

Examination channel 894 also may have any suitable size. Channel 894 may have a diameter that is about the same as or larger than the diameter of droplet outlet channel 884. A greater diameter of the examination channel may cause the droplets to slow down before they reach examination region 874, which may permit more accurate measurements. Accordingly, examination channel 894 may have a diameter that is about the same as the diameter of droplets 876, to keep droplets centered in the channel as they pass through the examination region. In any event, the diameter of the examination region may be about one-half to two droplet diameters, among others. Generally, an examination region with a smaller diameter can improve detection uniformity because the positional variation of droplets laterally within the examination region is reduced. Also, an examination region with a smaller diameter (e.g., the diameter of the droplet or smaller) can reduce the ability of intact droplets to catch up with coalesced droplets, which may travel more slowly. Droplet outlet channel 884 and examination channel 894 may be formed by discrete structures, such as a connector and tubing, respectively (see below).

The distance between confluence region 886 and examination region 874 may be a compromise between droplet stabilization and droplet separation. If the examination region is too close to the confluence region, droplet shape may not have stabilized yet. On the other hand, if the examination region is too far from the confluence region, droplets may travel at different rates, which may cause droplets to cluster. In exemplary embodiments, the examination region is at least about five droplet diameters from the separation region and less than about 1000 droplet diameters away. Generally, the optimal distance between the confluence region and the examination region depends on the size of the droplet and the amount of shear stress generated by the dilution fluid in the confluence region.

Any suitable flow rates of the emulsion and dilution fluid may be used. The emulsion flow rate in the droplet inlet channel may depend on the viscoelastic stability of the droplets. Increased surface tension (liquid-liquid) or increased moduli (membrane) allow for higher shear on the droplets without rupture. Accordingly, droplets that have a higher viscoelastic stability, such as droplets encapsulated by a skin, may be substantially more stable to higher flow rates than those with a lower viscoelastic stability and/or without a skin. Further aspects of droplets encapsulated by a skin are described in U.S. patent application Ser. No. 12/976,827, filed Dec. 22, 2010, which is incorporated herein by reference. A suitable flow rate for the dilution fluid in dilution channels 882 depends on the diameter of the dilution channels, droplet size, diameter of the examination region, etc. Exemplary flow rates for the dilution fluid are about one-half to ten times the flow rate of the emulsion into the confluence region. Relatively higher flow rates may be advantageous in the removal of debris that can clog droplet inlet channel 880, tapered region 888 and/or uniform region 890 thereof. On the other hand, relatively higher flow rates can produce shear stresses that can reduce droplet integrity by causing droplets to either break up or coalesce. Low flow rates can reduce shear stress and in turn preserve droplet integrity but produce less droplet separation.

Droplet inlet channel 880 and dilution channels 882 may extend to confluence region 886 at any suitable angles. For example, the dilution channels may be substantially perpendicular to the droplet inlet channel or each may form an angle of about 30 to 90 degrees with the droplet inlet channel.

FIG. 19 shows a somewhat schematic embodiment of a cross-shaped spacer 910 that may be included in detection system 870 of FIG. 18. Spacer 910 may be formed by a discrete connector 912 that provides fluid communication between droplet inlet tubing 914, dilution inlet tubing 916, and droplet outlet tubing 918. Any of the tubing may be described as a tube and/or a capillary. Connector 912 may define at least a portion of droplet inlet channel 880 (particularly tapered region 888 uniform region 890), dilution inlet channels 882, droplet outlet channel 884, and separation region 886. Accordingly, inlet tubing 914 supplies droplets, dilution tubing 916 supplies a dilution fluid, and droplet outlet tubing 918 receives separated droplets and may carry the separated droplets to an examination region formed by the outlet tubing.

The connector also may define a counterbore 919 for each channel, with the counterbore sized to receive an end of a piece of tubing (i.e., tubing 914, 916, or 918) and a fitting 920. The counterbore may include an internal thread 922 that engages an external thread of the fitting to secure the tubing to the connector with a fluid-tight seal.

Connector 912 may be formed of any suitable material. In some embodiments, the connector may be formed of a polymer (plastic). The polymer may be hydrophobic or a hydrophobic coating may be added to surfaces of the channels. The connector may be formed by machining a block of material and a smooth finish may be formed on machined inner surfaces.

Outlet tubing 918 may form examination region 874 (see FIG. 18). Outlet tubing 918 of larger diameter may offer the advantage of lower resistance to flow, enabling the system to run at lower pressures, which can simplify the design and lower the cost of the system. In contrast, connector 912 may provide a "choke point," namely, a minimum diameter, where the diameter is less than the diameter of the outlet tubing (and/or inlet tubing). The use of a choke point can be advantageous because it simplifies the location of clogs and their removal. Also, placing the choke point in a discrete component, such as connector 912, permits removal of clogs by replacing and/or servicing only the component. On the other hand, outlet tubing of smaller diameter requires a lower singulation ratio (the ratio of the flow rates of the dilution fluid to the emulsion) because less dilution fluid and/or continuous phase is required between the droplets and the tubing wall.

Example 9

Detection System with a T-Shaped Spacer

Figure 20:
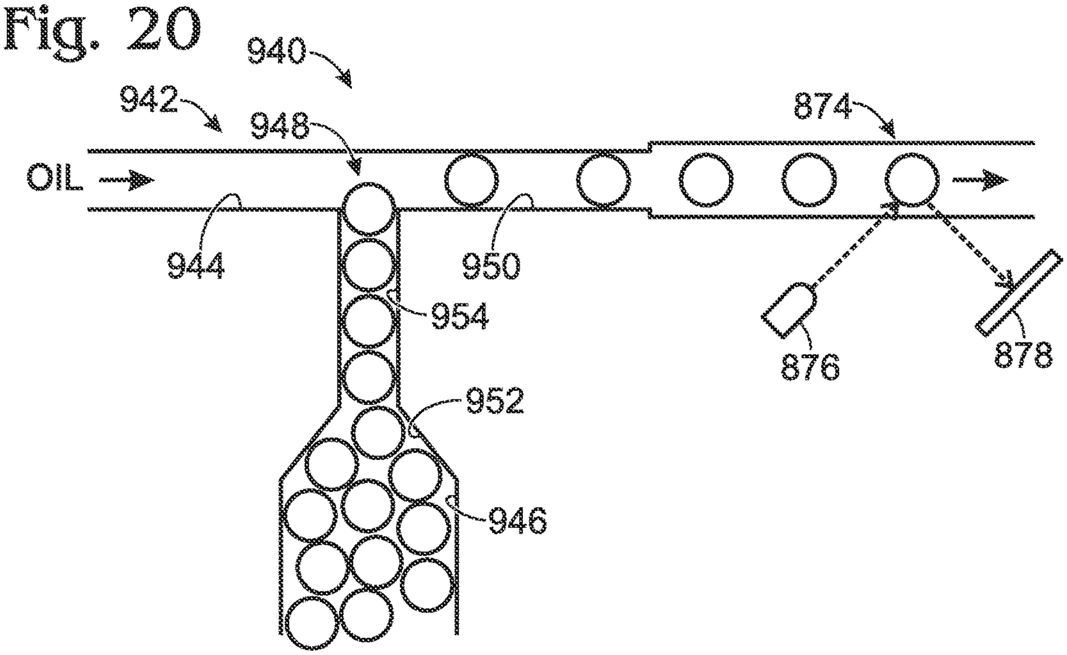
FIG. 20 is a schematic view of an exemplary detection system including a T-shaped spacer positioned upstream of an examination region, in accordance with aspects of the present disclosure.
Figure 21:
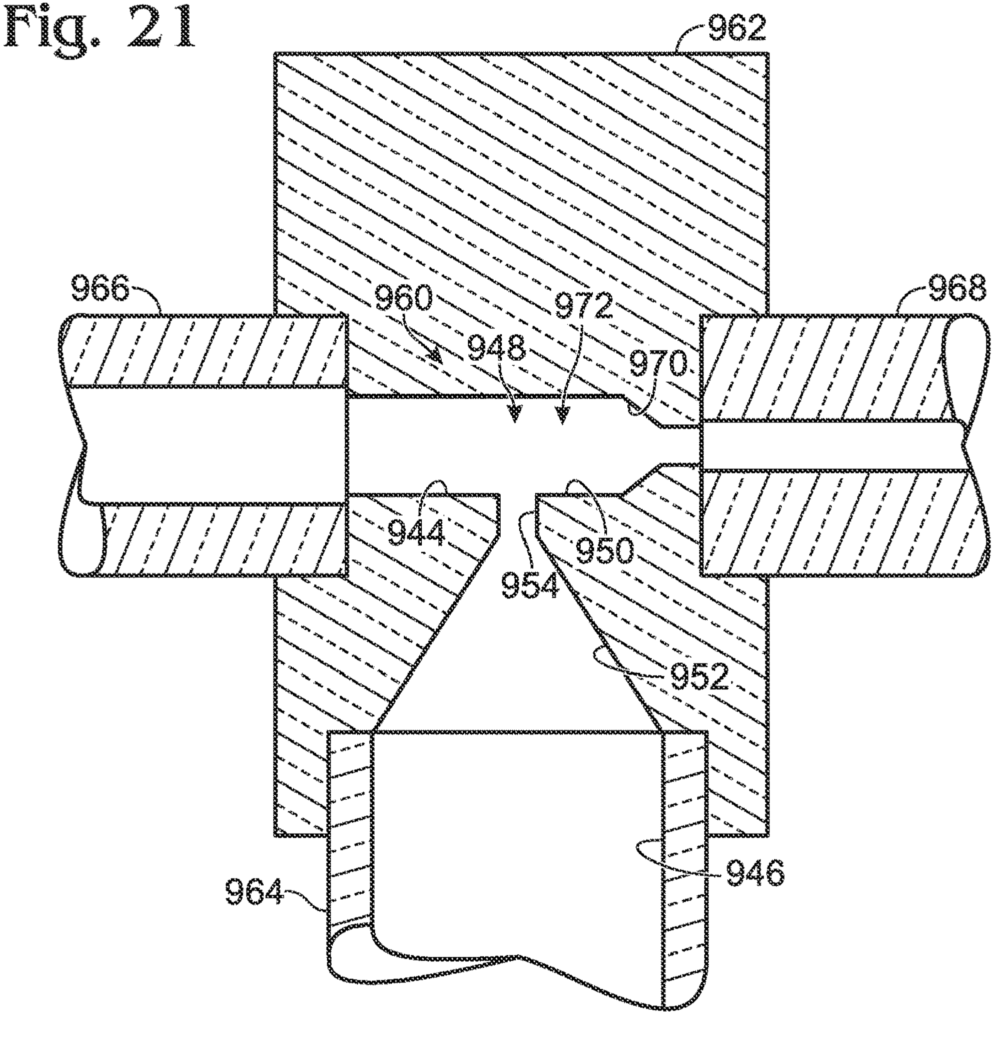
FIG. 21 is a sectional view of another exemplary T-shaped spacer that may be included in the detection system of FIG. 20, in accordance with aspects of the present disclosure.

This example describes an exemplary detection system including a T-shaped spacer; see FIGS. 20 and 21.

FIG. 20 shows an exemplary detection system 940 including a spacer 942 disposed upstream of examination region 874. The examination region is operatively connected to a light source 876 and a detector 874 as described above for detection system 870 of FIG. 18.

Spacer 942 may be structured and operates generally as described above for spacer 872 but differs in having only one dilution inlet channel 944, instead of two. Dilution channel 944 and a droplet inlet channel 946 meet at a confluence region 948 that joins a droplet outlet channel 950. Droplet inlet channel 946 may include a tapered region 952 and a uniform region 954, which may place droplets in single file. The dilution fluid may dilute the emulsion in the confluence region. Dilution channel 944 and droplet outlet channel 950 may or may not be coaxial. Also, droplet inlet channel 946 may join the dilution inlet channel and droplet outlet channel at any suitable angle including 90 degrees as shown here, or obliquely. Accordingly, spacer 942 may be described at being T-shaped, although the "T" may be distorted to be more Y-shaped in some embodiments.

FIG. 21 shows a somewhat schematic embodiment of a T-shaped spacer 960 that may be included in detection system 940 of FIG. 20. Spacer 960, like spacer 910 above (see FIG. 19), may be formed by a discrete connector 962. Connector 962 may have any of the properties or features described above for connector 912. (Fittings 920 have been omitted to simplify the presentation (see FIG. 19).) Connector 962 may provide fluid communication between droplet inlet tubing 964, dilution inlet tubing 966, and droplet outlet tubing 968. The connector may define at least a portion of dilution inlet channel 944, droplet inlet channel 946, confluence region 948, and droplet outlet channel 950. Here, droplet outlet channel 950 includes a tapered region 970 that tapers away from confluence region 948.

A region 972 of droplet outlet channel adjacent confluence region 948 may have a diameter that is at least 25% larger in diameter than the desired droplet size. This feature may cause any bolus of aqueous fluid entering the confluence region only to generate droplets that are significantly larger than the target droplet size. The T-shaped separator configuration may maintain significant force for separating droplets at up to two times the target droplet diameter. The exit constriction may be kept close to the introduction constriction so that any droplet that enters the droplet confluence region and region 972 will accelerate down the droplet outlet channel before the next droplet can enter the confluence region, effectively separating the droplets.

Example 10

Detection System with Serial Spacers

Figure 22:
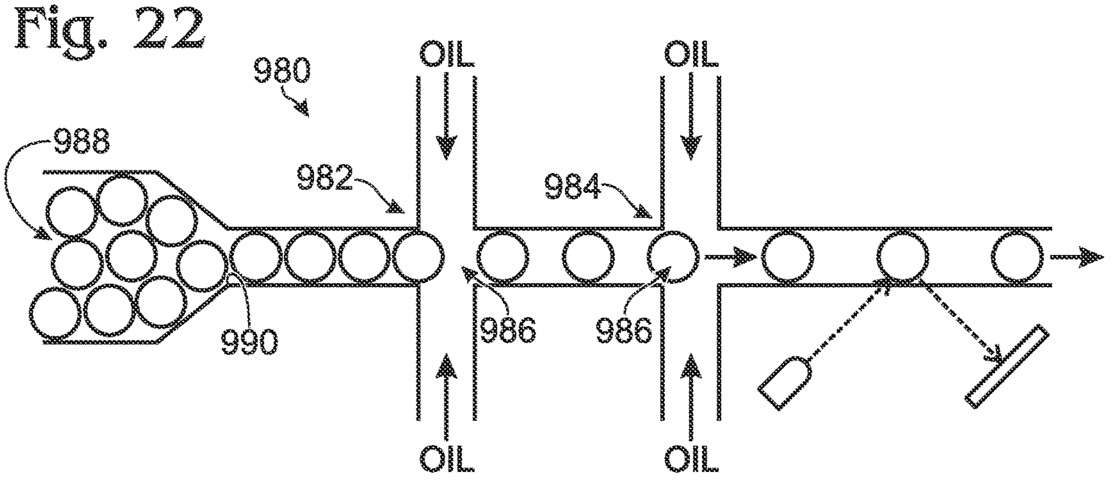
FIG. 22 is a schematic view of an exemplary detection system including multiple spacers arranged in series, in accordance with aspects of the present disclosure.
Figure 23:
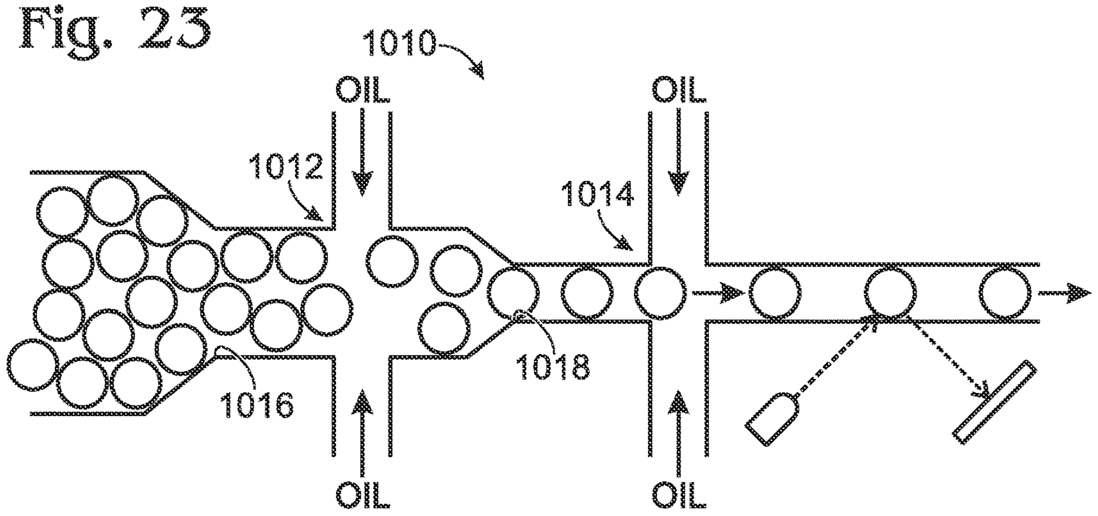
FIG. 23 is a schematic view of another exemplary detection system including multiple spacers arranged in series, in accordance with aspects of the present disclosure.
Figure 24:
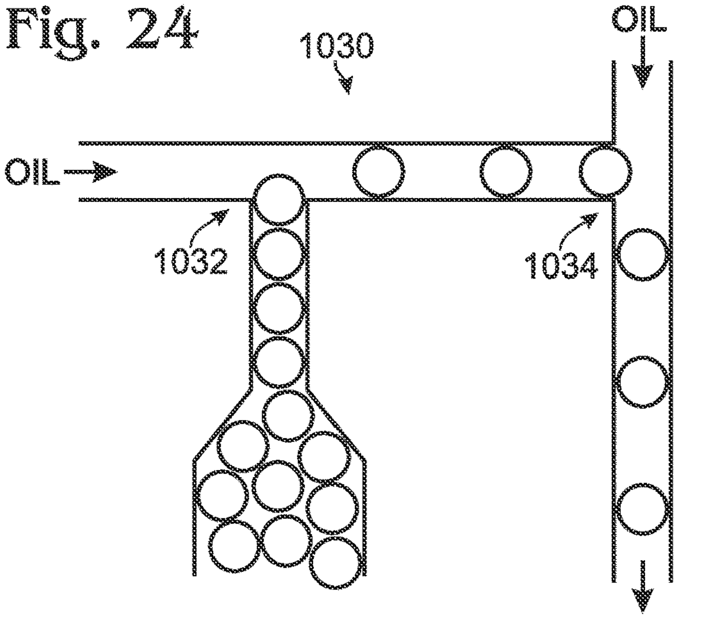
FIG. 24 is a schematic view of yet another exemplary detection system including multiple spacers arranged in series, in accordance with aspects of the present disclosure.

This example describes exemplary detection systems including serial spacers that increase the separation between droplets in two or more steps; see FIGS. 22-24.

FIG. 22 shows an exemplary detection system 980 including serial spacers 982, 984. Detection system 980 reduces the shear force exerted on droplets at each confluence region 986 by arranging two or more spacers in series. Each spacer dilutes emulsion 988; the average distance between droplets increases in multiple steps. Here, spacer 982 includes a neck region 990 that arranges droplets in single file before the droplets are separated. Spacer 984 further increases the average distance between droplets.

FIG. 23 shows another exemplary detection system 1010 including multiple spacers 1012, 1014. Here, both spacers include respective neck regions 1016, 1018. With this arrangement, droplets may be transitioned from multiple file to single file in two or more steps.

FIG. 24 shows yet another exemplary detection system 1030 including multiple spacers 1032, 1034 arranged in series. Each spacer has only one dilution inlet channel and is T-shaped. In other embodiments, spacers with different numbers of dilution inlet channels may be combined. For example, a T-shaped spacer may be combined with a cross-shaped spacer.

Example 11

Selected Embodiments

This example describes additional aspects and features of systems for spacing of droplets and the detection of spaced droplets, presented without limitation as a series of numbered paragraphs. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

A. A droplet singulator, comprising (i) a droplet channel including a droplet inlet configured to receive droplets of sample fluid suspended in a carrier fluid; (ii) a shell surrounding at least a portion of the droplet channel; and (iii) a plurality of dilution channels formed within the shell and configured to transport dilution fluid to the droplet channel at a controlled rate.

A1. The droplet singulator of paragraph A, further comprising a dilution fluid input channel formed in the shell and configured to receive dilution fluid from a source disposed outside the shell.

A2. The droplet singulator of paragraph A, wherein the shell is cylindrical, further comprising a cylindrical frit disposed within the shell, the frit having porous walls and a central bore defining the portion of the droplet channel surrounded by the shell, and wherein the dilution channels are formed by the porous walls of the frit.

A3. The droplet singulator of paragraph A, further comprising a porous inner cylinder disposed within the shell, the porous inner cylinder having porous walls forming the dilution channels and a central bore defining the portion of the droplet channel surrounded by the shell.

A4. The droplet singulator of paragraph A3, wherein the inner cylinder is a capillary.

A5. The droplet singulator of paragraph A3, wherein the inner cylinder is a filter.

A6. The droplet singulator of paragraph A, further comprising an inner cylinder disposed within the shell, the inner cylinder having a central bore defining the portion of the droplet channel surrounded by the shell and a plurality of radial bores extending between the central bore and an outer surface of the inner cylinder, and wherein the dilution channels are formed by the radial bores.

A7. The droplet singulator of paragraph A, wherein the droplet singulator is modular, wherein a first module of the droplet singulator includes the shell, and wherein a second module of the droplet singulator includes a microfluidic "T" fitting into which the shell is disposed.

B. A detection system for droplet-based assays, comprising (i) a droplet channel including a droplet inlet; (ii) a droplet input tip configured to inject droplets suspended in a carrier fluid into the droplet inlet and to cause the suspended droplets to move through the droplet channel; (iii) a shell surrounding a portion of the droplet channel; (iv) a plurality of dilution channels formed inside the shell and configured to transport dilution fluid into the droplet channel at a controlled rate and thereby to increase an average distance between droplets disposed within the droplet channel; (v) a detection region disposed downstream from the dilution fluid input channel; and (vi) a detector configured to detect fluorescence radiation emitted by droplets passing through the detection region.

B1. The system of paragraph B, further comprising a dilution fluid input channel formed in the shell and configured to receive dilution fluid from a source disposed outside the shell.

B2. The system of paragraph B, further comprising a porous inner cylinder disposed within the shell, the porous inner cylinder having porous walls forming the dilution channels and a central bore defining a dilution region of the droplet channel.

B3. The system of paragraph B2, wherein the inner cylinder is a ceramic frit.

B4. The system of paragraph B2, wherein the inner cylinder is a capillary.

B5. The system of paragraph B2, wherein the inner cylinder is a filter.

B6. The system of paragraph B, further comprising an inner cylinder disposed within the shell, the inner cylinder having a plurality of radial bores forming the dilution channels and a central bore defining a dilution region of the droplet channel.

B7. The system of paragraph B, wherein the shell is configured to interface with a standard microfluidic "T" fitting.

C. A method of detecting radiation emitted by droplets in a droplet-based assay, comprising (i) transporting droplets of a sample fluid suspended in a carrier fluid into a droplet channel; (ii) transporting the droplets downstream through the droplet channel; (iii) transporting dilution fluid into a shell surrounding the droplet channel; (iv) transporting the dilution fluid from the shell into the droplet channel at a controlled rate through a plurality of dilution channels formed inside the shell, thereby increasing an average distance between droplets disposed within the droplet channel; (v) transporting the droplets to a detection region; and (vi) detecting fluorescence radiation emitted by droplets passing through the detection region.

C1. The method of paragraph C, wherein transporting the dilution fluid through a plurality of dilution channels includes transporting the dilution fluid through porous walls of a cylindrical frit disposed within the shell.

C2. The method of paragraph C, wherein transporting the dilution fluid through a plurality of dilution channels includes transporting the dilution fluid through porous walls of a capillary disposed within the shell.

C3. The method of paragraph C, wherein transporting the dilution fluid through a plurality of dilution channels includes transporting the dilution fluid a plurality of radial bores formed in an inner cylinder disposed within the shell.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A detection system for droplet-based assays, comprising a droplet channel including a droplet inlet configured to receive droplets suspended in a carrier fluid;

a shell surrounding a portion of the droplet channel and having an input channel therein;

a porous cylinder disposed within the shell and having a central bore that forms a portion of the droplet channel, the porous cylinder having porous walls that provide fluid communication between a periphery of the porous cylinder and the central bore;

a source of dilution fluid connected to the input channel and disposed outside the shell;

a detection channel in fluid communication with, and disposed downstream from, the droplet channel;

a light source to generate light that irradiates the detection channel;

one or more pumps operable to (a) drive travel of droplets and carrier fluid through the central bore and the detection channel and (b) force flow of dilution fluid into the central bore via the porous walls; and a detection region including a fluorescence detector and one or more optical elements, the one or more optical elements being configured to direct, to the fluorescence detector, fluorescence radiation emitted by droplets passing through the detection channel.

2. The system of claim 1, wherein the porous cylinder includes a frit.

3. The system of claim 1, wherein the porous cylinder includes a capillary.

4. The system of claim 1, wherein the porous cylinder includes a filter.

5. The system of claim 1, wherein the shell is configured to interface with a standard microfluidic “T” fitting.

6. The system of claim 1, further comprising a droplet input tip fluidically connected to the droplet channel and having an open bottom end configured to be placed into a container holding an emulsion, wherein one of the one or more pumps is configured to create a pressure differential that pulls droplets of the emulsion from the container into the tip via the open bottom end.

7. A detection system for droplet-based assays, comprising a droplet channel including a droplet inlet configured to receive droplets suspended in a carrier fluid;

a shell surrounding a portion of the droplet channel and having an input channel therein;

an annular frit disposed within the shell and having a central bore that forms a portion of the droplet channel, the annular frit having porous walls that provide fluid communication between a periphery of the annular frit and the central bore;

a source of dilution fluid connected to the input channel and disposed outside the shell;

a detection channel in fluid communication with, and disposed downstream from, the droplet channel;

a light source to generate light that irradiates the detection channel;

one or more pumps operable to (a) drive travel of droplets and carrier fluid through the central bore and the detection channel and (b) force flow of dilution fluid into the central bore via the porous walls; and a detection region including a fluorescence detector and one or more optical elements, the one or more optical elements being configured to direct, to the fluorescence detector, fluorescence radiation emitted by droplets passing through the detection channel.

8. The detection system of claim 1, wherein the central bore of the porous cylinder has a uniform diameter that substantially matches a diameter of the droplets.

9. The detection system of claim 7, wherein the central bore of the annular frit has a uniform diameter that substantially matches a diameter of the droplets.

* * * * *